(12) United States Patent
Disney et al.

(10) Patent No.: US 10,011,598 B2
(45) Date of Patent: *Jul. 3, 2018

(54) SMALL MOLECULES TARGETING REPEAT R(CGG) SEQUENCES

(71) Applicant: THE SCRIPPS RESEARCH INSTITUTE, La Jolla, CA (US)

(72) Inventors: Matthew D. Disney, Jupiter, FL (US); Biao Liu, East Amherst, NY (US); Jessica L. Childs-Disney, Jupiter, FL (US); Wang-Yong Yang, Palm Beach Gardens, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/412,231

(22) Filed: Jan. 23, 2017

(65) Prior Publication Data

US 2017/0152261 A1 Jun. 1, 2017

Related U.S. Application Data

(63) Continuation of application No. 14/424,761, filed as application No. PCT/US2013/057515 on Aug. 30, 2013, now Pat. No. 9,550,769.

(60) Provisional application No. 61/694,977, filed on Aug. 30, 2012.

(51) Int. Cl.
| | |
|---|---|
| *A61K 31/4745* | (2006.01) |
| *C07D 471/04* | (2006.01) |
| *C07D 519/00* | (2006.01) |
| *A61K 31/475* | (2006.01) |
| *A61K 47/65* | (2017.01) |

(52) U.S. Cl.
CPC .......... *C07D 471/04* (2013.01); *A61K 31/475* (2013.01); *A61K 47/65* (2017.08); *C07D 519/00* (2013.01)

(58) Field of Classification Search
CPC .......................... C07D 471/04; A61K 31/4745
USPC ............................................ 546/70; 514/285
See application file for complete search history.

(56) References Cited

U.S. PATENT DOCUMENTS 9,550,769 B2 * 1/2017 Disney ................ C07D 471/04

* cited by examiner

*Primary Examiner* — Charanjit Aulakh
(74) *Attorney, Agent, or Firm* — Geoffrey K. Cooper; Thomas Fitting

(57) ABSTRACT

The invention provides a series of bioactive small molecules that target expanded r(CGG) repeats, termed r(CGG)$^{exp}$, that causes Fragile X-associated Tremor Ataxia Syndrome (FXTAS). The compound was identified by using information on the chemotypes and RNA motifs that interact. Specifically, 9-hydroxy-5,11-dimethyl-2-(2-(piperidin-1-yl)ethyl)-6H-pyrido[4,3-b]carbazol-2-ium, binds the 5'CGG/3'GGC motifs in r(CGG)$^{exp}$ and disrupts a toxic r(CGG)$^{exp}$-protein complex. Specifically, dimeric compounds incorporating two 9-hydroxyellipticine analog structures can even more potently bind the 5'CGG/3'GGC motifs in r(CGG)$^{exp}$ and disrupts a toxic r(CGG)$^{exp}$-protein complex. Structure-activity relationships (SAR) studies determined that the alkylated pyridyl and phenolic side chains are important chemotypes that drive molecular recognition of r(CGG) repeats, such as r(CGG)$^{exp}$. Importantly, the compound is efficacious in FXTAS model cellular systems as evidenced by its ability to improve FXTAS-associated pre-mRNA splicing defects and to reduce the size and number of r(CGG)$^{exp}$-protein aggregates.

17 Claims, 20 Drawing Sheets

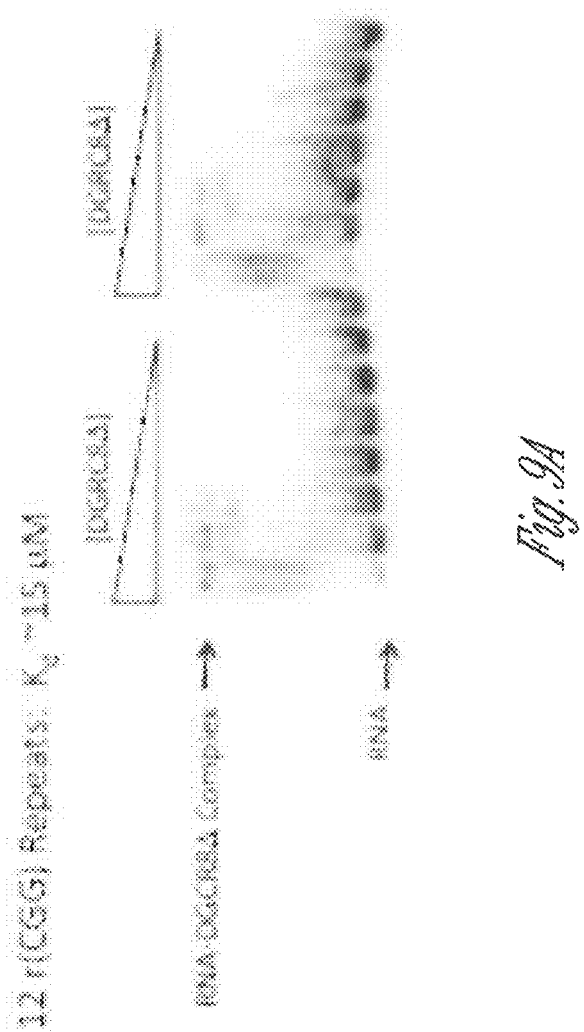

SEQUENCE LISTING

```
<160> NUMBER OF SEQ ID NOS: 20

<210> SEQ ID NO 1
<211> LENGTH: 28
<212> TYPE: RNA
<213> ORGANISM: Artificial Sequence
<220> FEATURE:
<223> OTHER INFORMATION: A synthetic oligoribonucleotide

<400> SEQUENCE: 1
aauuaauuaa uugaaaaauu aauuaauu                                          28

<210> SEQ ID NO 2
<211> LENGTH: 20
<212> TYPE: RNA
<213> ORGANISM: Artificial Sequence
```

-continued

```
<220> FEATURE:
<223> OTHER INFORMATION: A synthetic oligoribonucleotide

<400> SEQUENCE: 2
ggccggccga aaggccggcc                                                    20

<210> SEQ ID NO 3
<211> LENGTH: 46
<212> TYPE: RNA
<213> ORGANISM: Artificial Sequence
<220> FEATURE:
<223> OTHER INFORMATION: A synthetic oligoribonucleotide

<400> SEQUENCE: 3
gggagagggu uuaaucggua cgaaaguacg gauuggaucc gcaagg                       46

<210> SEQ ID NO 4
<211> LENGTH: 36
<212> TYPE: RNA
<213> ORGANISM: Artificial Sequence
<220> FEATURE:
<223> OTHER INFORMATION: A synthetic oligoribonucleotide

<400> SEQUENCE: 4
cggcggcggc ggcggcggcg gcggcggcgg cggcgg                                  36

<210> SEQ ID NO 5
<211> LENGTH: 20
<212> TYPE: DNA
<213> ORGANISM: Artificial Sequence
<220> FEATURE:
<223> OTHER INFORMATION: A synthetic primer

<400> SEQUENCE: 5
ggtgtccact cccagttcaa                                                    20

<210> SEQ ID NO 6
<211> LENGTH: 18
<212> TYPE: DNA
<213> ORGANISM: Artificial Sequence
<220> FEATURE:
<223> OTHER INFORMATION: A synthetic primer

<400> SEQUENCE: 6
gcctcaccac cgtgctgg                                                      18

<210> SEQ ID NO 7
<211> LENGTH: 21
<212> TYPE: DNA
<213> ORGANISM: Artificial Sequence
<220> FEATURE:
<223> OTHER INFORMATION: A synthetic primer

<400> SEQUENCE: 7
ggagctggtg gttgactttc t                                                  21

<210> SEQ ID NO 8
<211> LENGTH: 18
<212> TYPE: DNA
<213> ORGANISM: Artificial Sequence
<220> FEATURE:
<223> OTHER INFORMATION: A synthetic primer

<400> SEQUENCE: 8
tagaaggcac agtcgagg                                                      18
```

<210> SEQ ID NO 9
<211> LENGTH: 25
<212> TYPE: DNA
<213> ORGANISM: Artificial Sequence
<220> FEATURE:
<223> OTHER INFORMATION: A synthetic primer

<400> SEQUENCE: 9
gttcacaacc atctaaagca agatg                                           25

<210> SEQ ID NO 10
<211> LENGTH: 19
<212> TYPE: DNA
<213> ORGANISM: Artificial Sequence
<220> FEATURE:
<223> OTHER INFORMATION: A synthetic primer

<400> SEQUENCE: 10
gttgcatggc tggtgcagg                                                  19

<210> SEQ ID NO 11
<211> LENGTH: 30
<212> TYPE: DNA
<213> ORGANISM: Artificial Sequence
<220> FEATURE:
<223> OTHER INFORMATION: A synthetic primer

<400> SEQUENCE: 11
cggggtacca aatgctgcag ttgactctcc                                      30

<210> SEQ ID NO 12
<211> LENGTH: 29
<212> TYPE: DNA
<213> ORGANISM: Artificial Sequence
<220> FEATURE:
<223> OTHER INFORMATION: A synthetic primer

<400> SEQUENCE: 12
ccgctcgagc cattcatgaa gtgcacagg                                       29

<210> SEQ ID NO 13
<211> LENGTH: 34
<212> TYPE: DNA
<213> ORGANISM: Artificial Sequence
<220> FEATURE:
<223> OTHER INFORMATION: A synthetic primer

<400> SEQUENCE: 13
gtacaagctt gaatgctgct cctgtccaag acag                                 34

<210> SEQ ID NO 14
<211> LENGTH: 25
<212> TYPE: DNA
<213> ORGANISM: Artificial Sequence
<220> FEATURE:
<223> OTHER INFORMATION: A synthetic primer

<400> SEQUENCE: 14
gccctcgagc gtgggcacgc tggtc                                           25

<210> SEQ ID NO 15
<211> LENGTH: 20
<212> TYPE: DNA
<213> ORGANISM: Artificial Sequence
<220> FEATURE:
<223> OTHER INFORMATION: A synthetic primer

```
<400> SEQUENCE: 15
ggtgtccact cccagttcaa                                              20

<210> SEQ ID NO 16
<211> LENGTH: 18
<212> TYPE: DNA
<213> ORGANISM: Artificial Sequence
<220> FEATURE:
<223> OTHER INFORMATION: A synthetic primer

<400> SEQUENCE: 16
gcctcaccac cgtgctgg                                                18

<210> SEQ ID NO 17
<211> LENGTH: 25
<212> TYPE: DNA
<213> ORGANISM: Artificial Sequence
<220> FEATURE:
<223> OTHER INFORMATION: A synthetic primer

<400> SEQUENCE: 17
gttcacaacc atctaaagca agatg                                        25

<210> SEQ ID NO 18
<211> LENGTH: 19
<212> TYPE: DNA
<213> ORGANISM: Artificial Sequence
<220> FEATURE:
<223> OTHER INFORMATION: A synthetic primer

<400> SEQUENCE: 18
gttgcatggc tggtgcagg                                               19

<210> SEQ ID NO 19
<211> LENGTH: 30
<212> TYPE: DNA
<213> ORGANISM: Artificial Sequence
<220> FEATURE:
<223> OTHER INFORMATION: A synthetic primer

<400> SEQUENCE: 19
cggggtacca aatgctgcag ttgactctcc                                   30

<210> SEQ ID NO 20
<211> LENGTH: 29
<212> TYPE: DNA
<213> ORGANISM: Artificial Sequence
<220> FEATURE:
<223> OTHER INFORMATION: A synthetic primer

<400> SEQUENCE: 20
ccgctcgagc cattcatgaa gtgcacagg                                    29
```

SMALL MOLECULES TARGETING REPEAT R(CGG) SEQUENCES

CROSS-REFERENCE TO RELATED APPLICATION

This application claims the priority of U.S. provisional application Ser. No. 61/694,977, filed Aug. 30, 2012, the disclosure of which is incorporated herein by reference in its entirety.

STATEMENT OF GOVERNMENT SUPPORT

This invention was made with government support under grant numbers 3R01GM079235-02S1 and 1R01GM079235-01A2, awarded by the National Institutes of Health. The U.S. government has certain rights in the invention.

BACKGROUND

The development of small molecule chemical probes or therapeutics that target RNA remains a significant challenge despite the great interest in such compounds. The most significant barrier to compound development is a lack of knowledge of the chemical and RNA motif spaces that interact specifically.

RNA plays diverse and important roles in biological processes (1). Aberrant RNA function causes many severe diseases (2). For example, microRNA disregulation can contribute to cancer (3) and single nucleotide mutations in mRNAs cause beta-thalassemia and inherited breast cancer (4). RNA trinucleotide repeat expansions (termed $r(NNN)^{exp}$ where each rN signifies a ribonucleotide of the repeated sequence) cause various neurological disorders (5) including Fragile X Syndrome (FXS), Fragile X-associated Tremor Ataxia Syndrome (FXTAS), myotonic dystrophy type 1 (DM1), and Huntington's disease (HD).

Although RNA transcripts with expanded repeats cause the diseases mentioned above, the physiological response to the repeats and thus the causes of disease are quite different. Differences are mainly due to the location of the expanded repeats in a given mRNA. For example, HD is caused by an expansion of r(CAG) in the coding region of huntingtin mRNA. In the most well established mechanism of HD, disease is caused when expanded r(CAG) repeats are translated into a toxic polyQ version of huntingtin (6). Thus, HD is caused by a gain-of-function at the protein level. In FXS, >200 copies of r(CGG) in the 5' untranslated region (UTR) of the fragile X mental retardation 1 (FMR1) mRNA causes disease by recruiting the 'RNA-induced initiator of transcriptional gene silencing' (RITS) complex. The RITS complex then recruits DNA methyltransferase(s) (DMTases) and/or histone methyltransferases (HMT) to initiate local methylation of the FMR1 gene, causing transcriptional silencing (7). Thus, FXS is caused by a loss-of-function. Lastly, FXTAS and DM1 are caused when expanded repeats present in UTR's sequester proteins that are involved in pre-mRNA splicing regulation (8, 9). Sequestration of these proteins causes the aberrant splicing of a variety of pre-mRNAs, leading to the expression of defective proteins. Thus, FXTAS and DM1 are caused by an RNA gain-of-function.

FXTAS is a late onset (over age 50) neurological condition that affects balance, tremor, and memory. It affects 1 in 3000 men and 1 in 5000 women. FXTAS is caused by expanded CGG-repeat (55-200) alleles in the 5' untranslated region (UTR) of the fragile X mental retardation 1 (FMR1) gene located on the X chromosome. Gain-of-function of $r(CGG)^{exp}$ is a general pathogenic mechanism of FXTAS similar to myotonic dystrophy. Evidence for RNA gain-of-function comes from animal models and cell-based assays. For example, insertion of untranslated $r(CGG)^{exp}$ of the length that cause FXTAS into mice and *Drosophila* cause deleterious effects like those observed in humans that have FXTAS. In cell-based models, $r(CGG)^{exp}$ form nuclear inclusions, and the size of inclusions scales with the length of the repeat and the age of death from the disease.

A more detailed mechanism for the RNA gain-of-function has recently been elucidated from studies of patient-derived tissues and model cell lines. In studies by the Charlet group, it was shown that $r(CGG)^{exp}$ first recruits DGCR8 followed by recruitment of the Src-Associated substrate during mitosis of 68 kDa (Sam68) protein. The RNA-protein complex is a scaffold for the assembly of other proteins such as muscleblind-like 1 protein (MBNL1) and heterogeneous nuclear ribonucleoprotein (hnRNP). Sam68 is a nuclear RNA-binding protein involved in alternative splicing regulation, and the sequestration of Sam68, MBNL1, and hnRNP by $r(CGG)^{exp}$ leads to the pre-mRNA splicing defects observed in FXTAS patients (see FIG. 1). Targeting $r(CGG)^{exp}$ to inhibit DGCR8 and Sam68 binding is an attractive treatment for FXTAS.

Despite the contribution of expanded RNA repeats to diseases, there are few compounds that target these RNAs in particular and non-ribosomal RNAs in general. Our group recently reported two approaches to design of small molecules (10, 11) and modularly assembled compounds (12) that bind RNA and modulate its function in vivo. In particular, we have used information about RNA motif-small molecule interactions (13-5) and chemical similarity searching (16-19) to design bioactive ligands that target $r(CUG)^{exp}$ and $r(CAG)^{exp}$, which cause DM1 and HD, respectively (10-12).

SUMMARY

The present invention is directed, in various embodiments, to materials and methods that can interfere with a binding interaction between a pathological form of messenger RNA (mRNA) that incorporated extended repeat r(CGG) sequences (termed $r(CGG)^{exp}$), i.e., ribonucleotide sequences wherein the trinucleotide cytosine-guanine-guanine is present in multiple adjacent repeats, and one or more protein that binds to, or is sequestered by, this structural motif. Extended ribonucleotide COO sequences are believed to form hairpin loops containing non-Watson-Crick G-G base pairs. Compounds and methods of the invention can be used to block this binding or sequestration interaction between the $r(CGG)^{exp}$ and proteins, such as proteins that would normally carry out mRNA splicing of exons to yield mature translatable RNA. This $r(CGG)^{exp}$ motif is associated with the genetic disease Fragile X-associated Tremor and Ataxia Syndrome (FXTAS), and compounds and methods of the invention can be used for treatment of this medical condition in patients afflicted therewith.

In various embodiments, the invention provides a r(CGG) binding compound of formula (I)

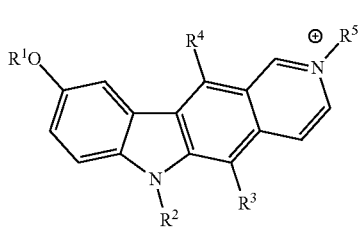

(I)

$R^1$ is H, (C1-C6)alkyl, or (C1-C6)alkanoyl;
$R^2$ is H, (C1-C6)alkyl, or (C1-C6)alkanoyl;
$R^3$ and $R^4$ are independently H, (C1-C6)alkyl, (C1-C6) haloakyl, (C1-C6)alkoxyalkyl (C1-C6)haloalkoxyalkyl, or (C6-C10)aryl;

R⁵ is (C1-C6)alkyl, (C1-C6)alkoxy(C1-C6)alkyl, (C1-C6)haloalkyl, (C1-C6)haloalkoxy, aryl(C1-C6)alkyl, heterocyclyl(C1-C6)alkyl, heteroaryl(C1-C6)alkyl, or (R⁶)₂N—(C1-C6)alkyl, wherein R⁶ is H or (C1-C6)alkyl;

wherein any alkyl, alkanoyl, alkoxy, aryl, heterocyclyl, or heteroaryl can be substituted with 0-3 J groups, wherein J is any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, R₂N, R₂NC(O), R₂NC(O)O, R₂NC(O)NR, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl;

R is independently at each occurrence H, (C1-C6)alkyl, or (C6-C10)aryl, wherein any alkyl or aryl group is substituted with 0-3 J;

provided the compound of formula (I) is not any of

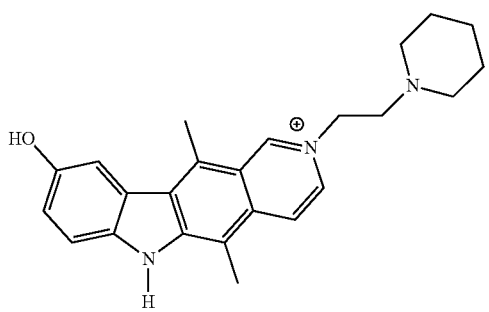

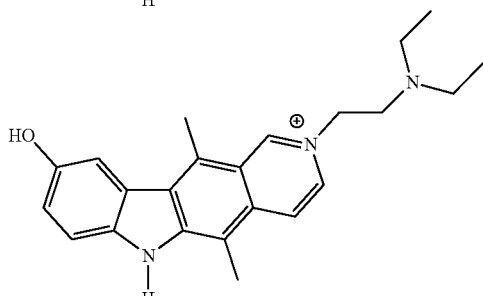

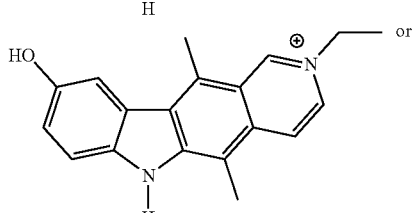

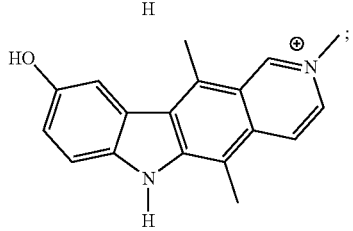

or a pharmaceutically acceptable salt thereof. A compound comprising only the single ellipticine scaffold, such as a compound of formula (I), is termed a monomeric compound herein. The monomeric compounds of the invention can be analogs of 9-hydroxyellipticine. In various embodiments, a compound of the invention is an analog of 9-hydroxyellipticine bearing an N-substituted pyridinium moiety.

In various embodiments, the invention also provides a dimeric r(CGG) binding compound of formula (I)

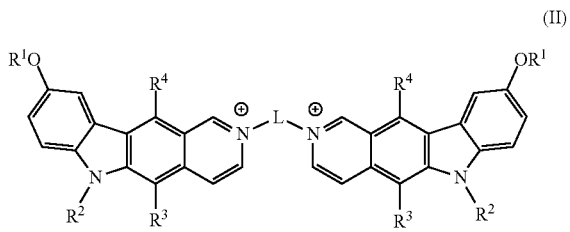

(II)

wherein R¹, R², R³, and R⁴ are as defined for the monomeric compound of formula (I), and wherein L is a linker comprising a polypeptide backbone bonded by two respective nitrogen atoms thereof to a nitrogen atom of a respective 1,2,3-triazole group via a respective (C1-C6)alkylene group optionally further comprising a glycyl residue, each respective triazole group being bonded via a (C1-C6)alkylene group to the respective pyridinium nitrogen atom of each ellipticine scaffold; or a pharmaceutically acceptable salt thereof; or a pharmaceutically acceptable salt thereof.

In various embodiments, the dimeric r(CGG) binding compound of formula (II) can comprise a linker of formula (LI)

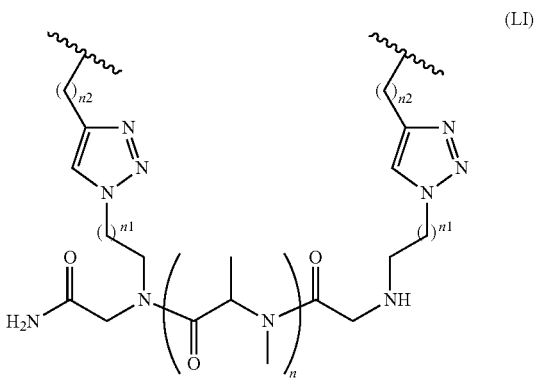

(LI)

wherein n=1, 2, 3, 4, 5, 6, 7, or 8; each independently selected n1=0, 1, 2, 3, 4, or 5; and each independently selected n2=1, 2, 3, 4, 5, or 6; and wherein a wavy line indicates a position of bonding to the respective pyridinium nitrogen atom of formula (II).

In various embodiments, the invention provides pharmaceutical composition comprising a compound of the invention and a pharmaceutically acceptable excipient.

In various embodiments, the invention provides a method of inhibiting a messenger RNA molecule with repeat r(CGG) sequence, for example wherein the repeat r(CGG) sequence is a r(CGG)$^{exp}$ sequence, from binding to a protein with a binding affinity for a RNA hairpin loop comprising a non-Watson-Crick G-G nucleotide pair, comprising contacting the messenger RNA molecule having the repeat r(CGG), e.g., an expanded r(CGG) (r(CGG)$^{exp}$), sequence, and an effective amount or concentration of a compound of formula (I)

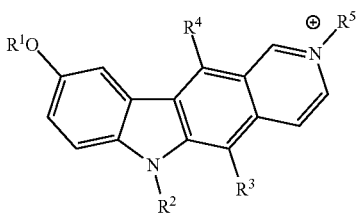

wherein
R¹ is K, (C1-C6)alkyl, or (C1-C6)alkanoyl;
R² is H, (C1-C6)alkyl, or (C1-C6)alkanoyl;
R³ and R⁴ are independently H, (C1-C6)alkyl, (C1-C6)haloalkyl, (C1-C6)alkoxyalkyl (C1-C6)haloalkoxyalkyl, or (C6-C10)aryl;
R⁵ is (C1-C6)alkyl, (C1-C6)alkoxy(C1-C6)alkyl, (C1-C6)haloalkyl, (C1-C6)haloalkoxy, aryl(C1-C6)alkyl, heterocyclyl(C1-C6)alkyl, heteroaryl(C1-C6)alkyl, or (R⁶)₂N—(C1-C6)alkyl, wherein R⁶ is H or (C1-C6)alkyl;
wherein any alkyl, alkanoyl, alkoxy, aryl, heterocyclyl, or heteroaryl can be substituted with 0-3 J groups, wherein J is any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, R₂N, R₃NC(O), R₂NC(O)O, R₂NC(O)NR, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl;
R is independently at each occurrence H, (C1-C6)alkyl, or (C6-C10)aryl, wherein any alkyl or aryl group is substituted with 0-3 J; or,
an effective amount or concentration of a dimeric r(CGG) binding compound of formula (I)

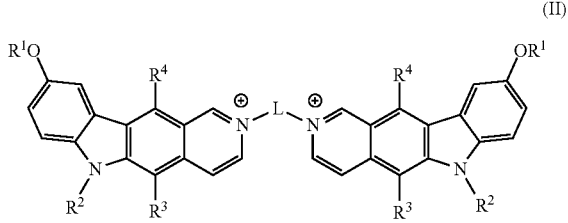

wherein R¹, R², R³, and R⁴ are as defined for the monomeric compound of formula (I), and wherein L is a linker comprising a poly(N-methylalanine) peptide backbone bonded by two respective nitrogen atoms thereof to a nitrogen atom of a respective 1,23-triazole group via a (C1-C6)alkylene group optionally further comprising a glycyl residue, each respective triazole group being bonded via a (C1-C6)alkylene group to the respective pyridinium nitrogen atom of the respective 9-hydroxyellipticine analogous moiety; or a pharmaceutically acceptable salt thereof; or a pharmaceutically acceptable salt thereof; or an effective dose of a pharmaceutical composition comprising a compound as described and a pharmaceutically acceptable excipient.
In various embodiments, the invention provides a method of inhibiting a messenger RNA molecule with an repeat r(CGG) sequence, such as an expanded r(CGG) sequence (termed a r(CGG)$^{exp}$ sequence herein) from binding to a protein with a binding affinity for a RNA hairpin loop comprising a non-Watson-Crick O-G nucleotide pair, comprising contacting the messenger RNA molecule having the repeat r(CGG) sequence, and an effective amount or concentration of an analog of 9-hydroxyellipticine comprising an N-substituted pyridinium moiety.
Accordingly, in various embodiments, the invention provides a method of treatment of Fragile X-associated Tremor Ataxia Syndrome, comprising administering to a patient afflicted therewith a therapeutically effective dose of a compound of formula (I)

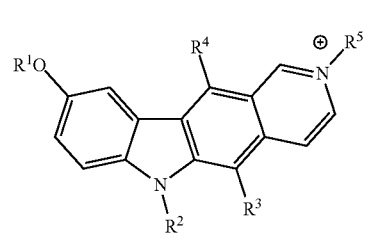

wherein
R¹ is H, (C1-C6)alkyl, or (C1-C6)alkanoyl;
R² is H, (C1-C6)alkyl, or (C1-C6)alkanoyl;
R³ and R⁴ are independently H, (C1-C6)alkyl, (C1-C6)haloalkyl, (C1-C6)alkoxyalkyl (C1-C6)haloalkoxyalkyl, or (C6-C10)aryl;
R⁵ is (C1-C6)alkyl, (C1-C6)alkoxy(C1-C6)alkyl, (C1-C6)haloalkyl, (C1-C6)haloalkoxy, aryl(C1-C6)alkyl, heterocyclyl(C1-C6)alkyl, heteroaryl(C1-C6)alkyl, or (R⁶)₂N—(C1-C6)alkyl, wherein R6 is H or (C1-C6)alkyl;
wherein any alkyl, alkanoyl, alkoxy, aryl, heterocyclyl, or heteroaryl can be substituted with 0-3 J groups, wherein J is any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, R₂N, R₂NC(O), R₂NC(O)O, R₂NC(O)NR, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl;
R is independently at each occurrence H, (C1-C6)alkyl, or (C6-C10)aryl, wherein any alkyl or aryl group is substituted with 0-3 J;
or a pharmaceutically acceptable salt thereof; or,
an effective amount or concentration of a dimeric r(CGG) binding compound of formula (B)

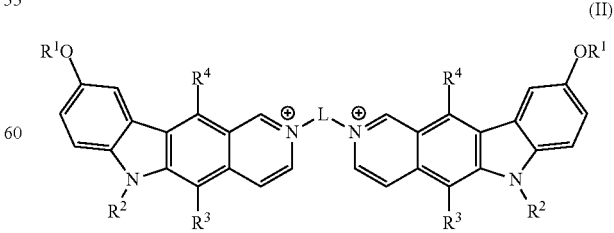

wherein R¹, R², R³, and R are as defined for the monomeric compound of formula (I), and wherein L is a linker comprising a poly(N-methylalanine) peptide backbone bonded by two respective nitrogen atoms thereof to a nitrogen atom of a respective 1,2,3-triazole group via a (C1-C6)alkylene group optionally further comprising a glycyl residue, each respective triazole group being bonded via a (C1-C6)alkylene group to the respective pyridinium nitrogen atom of the respective 9-hydroxyellipticine analogous moiety; or a pharmaceutically acceptable salt thereof;

or an effective dose of a pharmaceutical composition comprising a compound as described and a pharmaceutically acceptable excipient.

In various embodiments, the invention provides a method of treatment of Fragile X-associated Tremor Ataxia Syndrome, comprising administering to a patient afflicted therewith a therapeutically effective dose of an analog of 9-hydroxyellipticine comprising an N-substituted pyridinium moiety, or a dimeric derivative of 9-hydroxyellipticine wherein two 9-hydroxyellipticine scaffolds are linked via a linker group.

BRIEF DESCRIPTION OF THE FIGURES

FIG. 6B, 1a improves SMN2 pre-mRNA splicing defects. FIG. 6C, 1a improves Bcl-x pre-mRNA splicing defects.

FIG. 7A, shows confocal microscopy images of cells treated with different concentrations of 1a. For all panels: left, GFP fluorescence (indicates transfected cells); middle, Cy3 fluorescence (indicates $r(CGG)^{exp}$); right: overlay of GFP, Cy3, and DAPI (indicates nuclei) fluorescence images. Bottom, FIG. 7B, shows a plot of the number of r(CGG) aggregates as a function of the concentration of 1a.

FIGS. 8A and 88B show the $IC_{50}$ curve for displacement of DGCR8Δ from r(CGG)12 by compounds FIG. 8A: compound 1a, and FIG. 8B: compound 1b.

FIGS. 9A, 9B, and 9C show results of the Gel Mobility Shift Assays, showing that DGCR8Δ binds to RNAs with different numbers of r(CGG) repeats similarly; FIG. 9A: 12 c(CGG) repeats, FIG. 9B: 24 c(CGG) repeats; FIG. 9C: 60 c(CGG) repeats.

FIG. 10A, the GC internal loop RNA containing one 5'CGG/3'GGC motif; FIG. 10B: affinity of compound 1a as evidenced by FRET analysis; FIG. 10C: affinity of compound 1b as evidenced by FRET analysis.

FIGS. 1A and 11B show: FIG. 11B: a graphical plot related to the non-effect of compound 1a on splicing of a PLEKHH2 mini-gene.

FIG. 12A: a gel electrophoresis autoradiogram, and FIG. 12B: a graphical plot related to the non-effect of compound 1a on splicing of a cTNT mini-gene.

FIGS. 13A and 13B show synthetic schemes for: FIG. 13A: the E-alkyne compound, and FIG. 13B compound 2E-nNMe, as described further in the text.

FIG. 15A: a graph showing reduction of pre-mRNA splicing defects of SMN2 minigene figure with compound 2E-NMe; 15B: In vivo efficacy of 2E-5NMe against FXTAS as assessed by improvement in cTNT pre-mRNA splicing defects; 15C: In vive efficacy of 2E-5NMe against FXTAS as assessed by improvement in SMN2 pre-mRNA splicing defects.

DETAILED DESCRIPTION

Definitions

Figure 1:
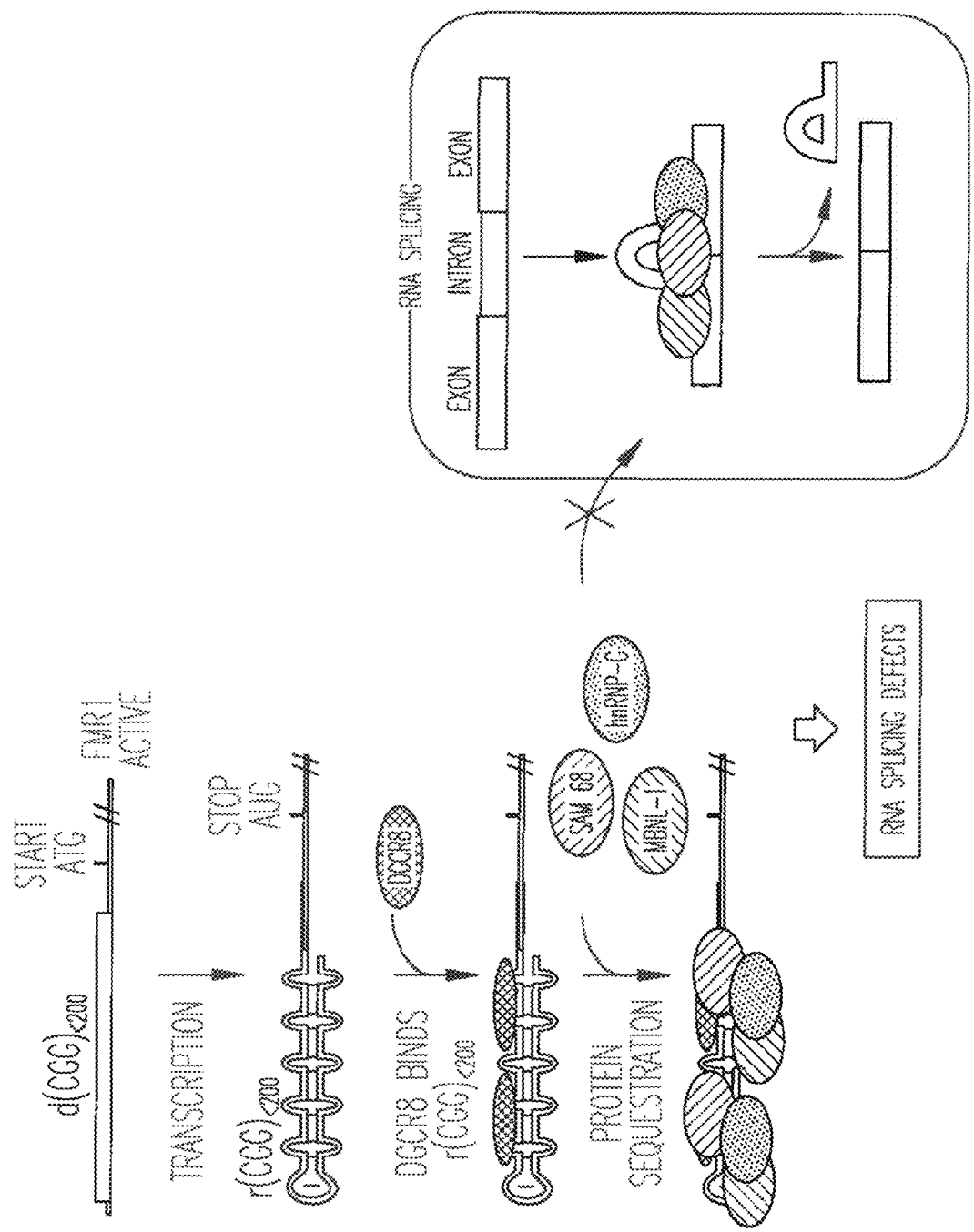
FIG. 1 shows a schematic of the pathogenic mechanism in FXTAS.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

Aspects of the present disclosure employ, unless otherwise indicated, techniques of chemistry, and the like, which are within the skill of the art. Such techniques are explained fully in the literature. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "condition" or "malcondition" are used interchangeably, and are used to refer to diseases or conditions wherein a repeat r(CGG) sequence, such as $r(CGG)^{exp}$, plays a role in the biochemical mechanisms involved in the disease or malcondition or symptom(s) thereof such that a therapeutically beneficial effect can be achieved by acting on a repeat r(CGG) sequence such as $r(CGG)^{exp}$. "Acting on" a repeat r(CGG) sequence, or "modulating" a repeat r(CGG) sequence, can include binding to a repeat r(CGG) sequence, and/or inhibiting the bioactivity of a repeat r(CGG) sequence, and/or blocking the interaction of a repeat r(CGG) sequence with proteins in vivo. The r(CGG) sequence can be a $r(CGG)^{exp}$ sequence.

The term "$r(CGG)^{exp}$" as used herein refers to a pathological form of messenger RNA (mRNA) that incorporated extended repeats of r(CGG) sequences (termed $r(CGG)^{exp}$), i.e., ribonucleotide sequences wherein the trinucleotide cytosine-guanine-guanine is present in multiple adjacent repeats; or to those domains of the messenger RNA comprising the extended r(CGG) repeats, depending upon context. The term "r(CGG)" refers to the ribonucleotide cytosine-guanine-guanine, as is found in ribonucleic acids (RNA), and a "repeat r(CGG) sequence" is a polyribonucleotide sequence with one or more tandem repeat of the r(CGG) triplet.

The expression "effective amount", when used to describe therapy to an individual suffering from a disorder, refers to the amount of a compound of the invention that is effective to inhibit or otherwise act on a repeat r(CGG) sequence such as $r(CGG)^{exp}$ in the individual's tissues wherein the repeat r(CGG) sequence such as $r(CGG)^{exp}$ involved in the disorder is active, such as e.g. in binding of translation or splicing related proteins, wherein such inhibition or other action occurs to an extent sufficient to produce a beneficial therapeutic effect, e.g., by blocking the effect of that protein-mRNA interaction.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

A "small molecule" refers to an organic compound, including an organometallic compound, of a molecular weight less than about 2 kDa, that is not a polynucleotide, a polypeptide, a polysaccharide, or a synthetic polymer composed of a plurality of repeating units.

As to any of the groups described herein, which contain one or more substituents, it is understood that such groups do not contain any substitution or substitution patterns that are sterically impractical and/or synthetically non-feasible. In addition, the compounds of this disclosed subject matter include all stereochemical isomers arising from the substitution of these compounds.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, alkynyl, azido, and halogen groups.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above. Aryl groups can also bear fused rings, such as fused cycloalkyl rings, within the meaning herein. For example, a tetrahydronaphthyl ring is an example of an aryl group within the meaning herein. Accordingly, an aryl ring includes, for example, a partially hydrogenated system, which can be unsubstituted or substituted, and includes one or more aryl rings substituted with groups such as alkyl, alkoxyl, cycloalkyl, cycloalkoxyl, cycloalkylalkyl, cycloalkoxyalkyl, and the like, and also fused with, e.g., a cycloalkyl ring.

Aralkyl or arylalkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. The sulfur S can be in various oxidized forms, such as sulfoxide S(O) or sulfone $S(O)_2$. Thus a heterocyclyl can be a cycloheteroalkyl or a heteroaryl, or if polycyclic, any combination thereof. In some embodiments, heterocyclyl groups include 3 to about 20 ring members, whereas other such groups have 3 to about 15 ring members.

Heterocyclyl groups can be monocyclic, or polycyclic, such as bicyclic, tricyclic, or higher cyclic forms. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzodioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, thiadiazolyl, pyridinyl, pyrimidinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

In general, "substituted", as in a "substituted" group (e.g., alkyl, aryl, etc.) refers to an organic group (alkyl, aryl, etc.) as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF, R', O (oxo), S (thiono), methylenedioxy, ethylenedioxy. N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')CO', N(OR)', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl.

In various embodiments, J is any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, R$_2$N, R$_2$NC(O), R$_2$NC(O)O, R$_2$NC(O)NR, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl; wherein R is independently at each occurrence H, (C1-C6)alkyl, or (C6-C10)aryl, wherein any alkyl or aryl group is substituted with 0-3 J.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene. T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Aloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-metboxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

Standard abbreviations for chemical groups such as are well known in the art can be used herein, and are within ordinary knowledge; e.g., Me=methyl, Et=ethyl, i-Pr=isopropyl. Bu=butyl, t-Bu=tert-butyl, Ph=phenyl, Bn=benzyl, Ac=acetyl, Bz=benzoyl, and the like.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases that are compounds of the invention. Salts can be "pharmaceutically-acceptable salts." The term "pharmaceutically-acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid or carbamic acid groups, which can be hydrolyzed by endogenous esterases as are found in the bloodstream of humans and other mammals. Endogenous hydrolysis of a carboxylic ester provides an alcohol and an acid; endogenous hydrolysis of a carbamate yields an alcohol, and amine, and carbon dioxide (through decarboxylation of the carbamic acid). Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Description

Overview

All RNA trinucleotide repeats fold into a hairpin with periodically repeating 1×1 nucleotide internal loops in the stem (20). We therefore probed an RNA-focused small molecule library enriched with chemotypes that bind RNA 1×1 nucleotide internal loops, such as the 1×1 nucleotide GG internal loop in $r(CGG)^{exp}$. Since FXTAS is caused by sequestration of proteins that regulate pre-mRNA splicing, a high throughput protein-displacement assay was used to screen for inhibitors. From this library, a designer small molecule, 9-hydroxy-5,11-dimethyl-2-(2-(piperidin-1-yl) ethyl)-6H-pyrido[4,3-b]carbazol-2-ium, was identified. The compound binds tightly to 1×1 nucleotide GG loops and is efficacious in cell culture models of FXTAS. Specifically, it improves pre-mRNA splicing defects and reduces the size and number of $r(CGG)^{exp}$ nuclear foci. Thus, this compound may serve as a chemical probe to understand how $r(CGG)^{exp}$ causes FXS and FXTAS, for which there is no treatment. Collectively, these studies suggest that small molecules targeting traditionally recalcitrant RNA targets can be developed.

FXTAS is caused by a pathogenic mechanism in which there is a gain-of-function by an expanded r(CGG) repeat, or $r(CGG)^{exp}$ (20). Like other expanded RNA trinucleotide repeating transcripts, $r(CGG)^{exp}$ folds into a hairpin structure with regularly repeating 1×1 nucleotide internal loops, or 5'CGG/3'GGC motifs (FIG. 1) (21). FXTAS patients are carriers of pre-mutation alleles (55-200 repeats) and have increased FMR1 mRNA levels and normal or moderately low FMRP protein expression levels (22,23). Evidence for RNA gain-of-function comes from animal models and cell-based assays. For example, insertion of untranslated $r(CGG)^{exp}$ (of the length that cause FXTAS) into mice and Drosophila cause deleterious effects like those observed in humans that have FXTAS (24, 25). In particular, it has been shown that there is genetic interaction between $r(CGG)^{exp}$ and Pure mediates neurodegeneration (26). In cell-based models, $r(CGG)^{exp}$ forms nuclear inclusions, and the size of inclusions scales with the length of the repeat and the age of death from the disease (27, 28).

A more detailed mechanism for the RNA gain-of-function has recently been elucidated from studies of patient-derived cell lines. In studies by the Charlet group (8), it was shown that $r(CGG)^{exp}$ first recruits DGCR8 (29), followed by recruitment of the Src-Associated substrate during mitosis of 68 kDa protein (Sam68). The RNA-protein complex is a scaffold for the assembly of other proteins such as musclebind-like 1 protein (MBNL1) and heterogeneous nuclear ribonucleoprotein (hnRNP). Sam68 is a nuclear RNA-binding protein involved in alternative splicing regulation (30), and the sequestration of Sam68 by $r(CGG)^{exp}$ leads to the pre-mRNA splicing defects observed in FXTAS patients (20). Thus, targeting $r(CGG)^{exp}$ to inhibit protein binding is an attractive treatment for FXTAS. We therefore screened a library enriched in small molecules that are biased, or focused, for binding RNA to identify lead ligands that bind $r(CGG)^{exp}$.

In order to construct a library of small molecules that is enriched in compounds that have the potential to recognize RNA 1×1 nucleotide internal loops like the ones that are displayed in $r(CGG)^{exp}$ (FIG. 1), previously reported chemical similarity searches were employed (10, 11.). Those searches identified compounds that are similar to the bis-benzimidazole Hoechst 33258, 4',6-diamidino-2-phenylindole (DAPI), and pentamidine. This RNA-focused collection of small molecules contained two small molecules that improve defects that are associated with r(CAG)$^{exp}$ and r(CUG)$^{exp}$ in cell culture models of HD and DM1, respectively (10, 11). Thus, Hoechst-, pentamidine-, and DAPI-like compounds were screened to identify inhibitors of the r(CGG)-DGCR8 Δ protein complex.

Screening was completed using a time-resolved FRET assay that has been previously described for identifying inhibitors of the r(CUG)$^{exp}$-MBNL1 and r(CAG)$_{exp}$-MBNL1 complexes (FIG. 1) (10, 11). Briefly, a 5'-biotinylated RNA oligonucleotide containing 12 r(CGG) repeats is incubated with Hiss-tagged DGCR8Δ. The ligand of interest is then added, followed by addition of two antibodies that recognize the RNA (streptavidin-XL665) or DGCR8Δ (Tb labeled anti-His.). If the compound does not displace DGCR8Δ, then Tb and XL-665 are within close enough proximity to form a FRET pair. If, however, the ligand displaces the protein, then no FRET is observed.

Figure 2:
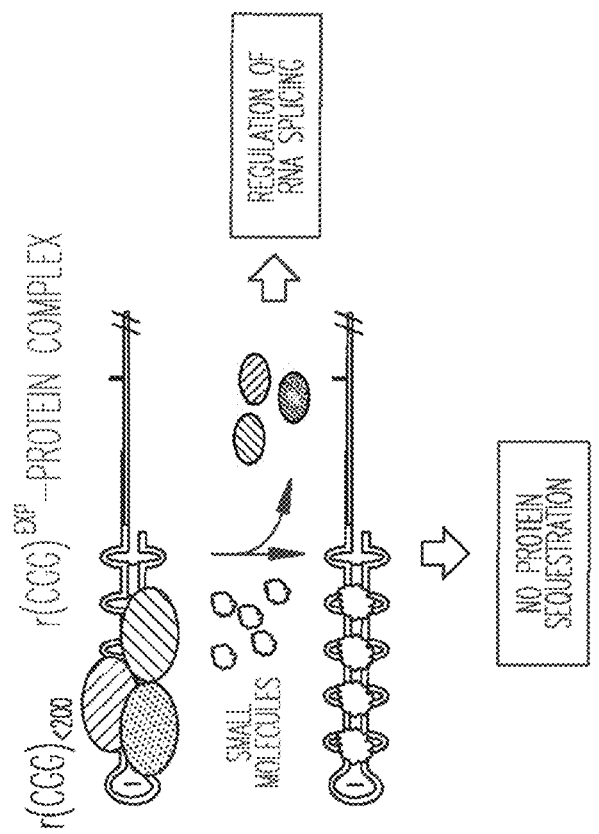
FIG. 2 shows a schematic strategy in treatment of FXTAS.

From this screen, three compounds (FIG. 2) were identified that disrupt the r(CGG)$^{exp}$-DGCR8Δ complex in the low to mid micromolar range. (Either no or very slight inhibition was observed for all other compounds at 100 μM). They include compounds 1a, 2, and Ht-N$_3$ (FIG. 2). Interestingly, all three compounds were derived from the Hoechst or bis-benzimidazole query. Dose-response curves show that 1a and Ht-Ns disrupt the r(CGG)$_{12}$-DGCR8Δ complex with IC$_{50}$'s of 12 and 33 μM, respectively. Compound 2, however, only disrupts ~25% of the r(CGG)$_{12}$-DGCR8Δ☐ complex at 100 μM.

Molecular Recognition of r(CGG)$^{exp}$ by 1a.

To further investigate the chemotypes in compound 1a that allow effective recognition of r(CO)$^{exp}$ and inhibition of the r(CGG)$_{12}$-DGCR8Δ complex, a series of derivatives were studied (FIG. 2). These compounds probe the role of: (i) the identity of the alkylated pyridyl side chain; (ii) the phenolic side chain; and, (iii) the positive charge. The IC$_{50}$ values for inhibition of protein binding for 1b, 1c, and 1d are similar to that of 1a (5-12 μM). The IC$_{50}$ of compound 1e is ~25 μM while 1f has no effect on protein binding at 25 μM. Table 1 summarizes the IC$_{50}$'s and the percentage of protein displaced from r(CGG)$_{12}$ at 25 μM of each compound. Taken together, the presence of a positive charge due to the alkylated pyridyl side chain and the presence of the exocyclic hydroxyl group are required for compound potency.

Figure 3:
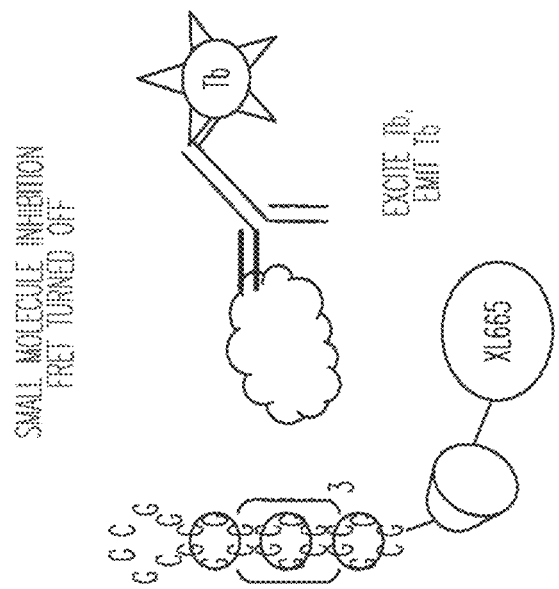
FIG. 3 shows a schematic of the protein displacement assay that was used to identify small molecule inhibitors of the $r(CGG)_{12}$-DGCR8Δ interaction and to determine their potencies. The $r(CGG)_{12}$ oligonucleotide is labeled with a 5'-biotin while DGCR8Δ (blue cloud) contains a histidine (His) tag. Left, in the absence of inhibitor, DGCR8Δ binds to $r(CGG)_{12}$. Binding is quantified by using two antibodies that form a FRET pair—an anti-His antibody labeled with Tb that binds to DGCR8Δ and streptavidin labeled with XL665 that binds to $r(CGG)_{12}$. The two fluorophores are within close enough proximity to form a FRET pair. Tb is excited at 345 nm; the resulting emission (~545 nm) excites XL665, which emits at 665 nm. Right, in the presence of inhibitor, the $r(CGG)_{12}$-DGCR8Δ interaction is disrupted, and the two fluorophores are not within close enough proximity to form a FRET pair. Therefore, emission is only observed at 545 nm (due to Tb). XL665 emission is not observed.
Figure 3:
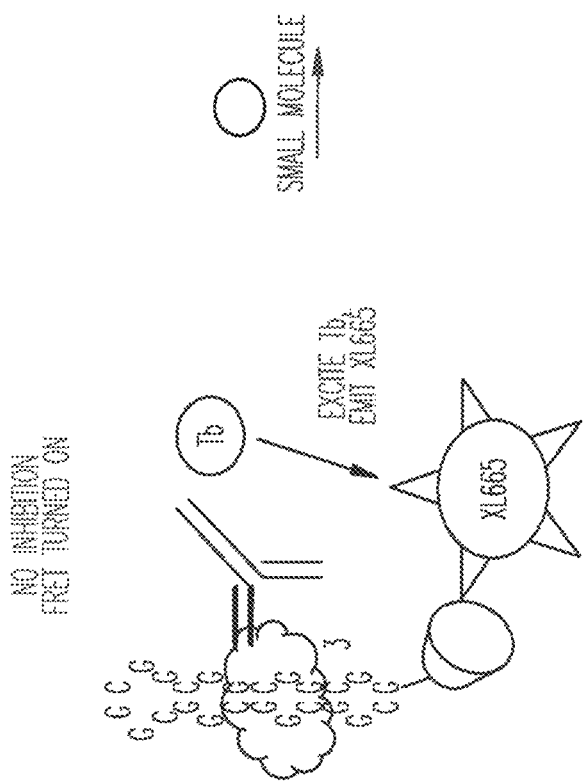

In the protein displacement assay, inhibition occurs if the small molecule binds the protein or the RNA. Therefore, we used competition dialysis (31) to assess the selectivity of 1a. A series of RNA targets, including two base paired RNAs, r(CGG)$_{12}$ (a mimic of r(CGG)$^{exp}$ used in the displacement assay, FIG. 1), and DGCR8Δ were used (FIG. 3). The results of these studies show that 1a binds tightly to r(CGG)$_{12}$ while very little binding is observed to DGCR8Δ. Although some binding is observed to fully paired RNAs, less than half of the amount of ligand that partitioned into r(CGG)$_{12}$ partitioned into these samples. Thus, 1a binds preferentially to r(CGG)$_{12}$ over the other targets tested. The binding affinities of 1a-1d for an RNA with a 1×1 nucleotide GG Internal loop motif were also determined. The measured K$_d$'s are similar for all four compounds and range from ~40-75 nM (Table 1), as expected based on their similar potencies.

Biological Activity of 1a in Model Cellular Systems of FXTAS.

Figure 4:
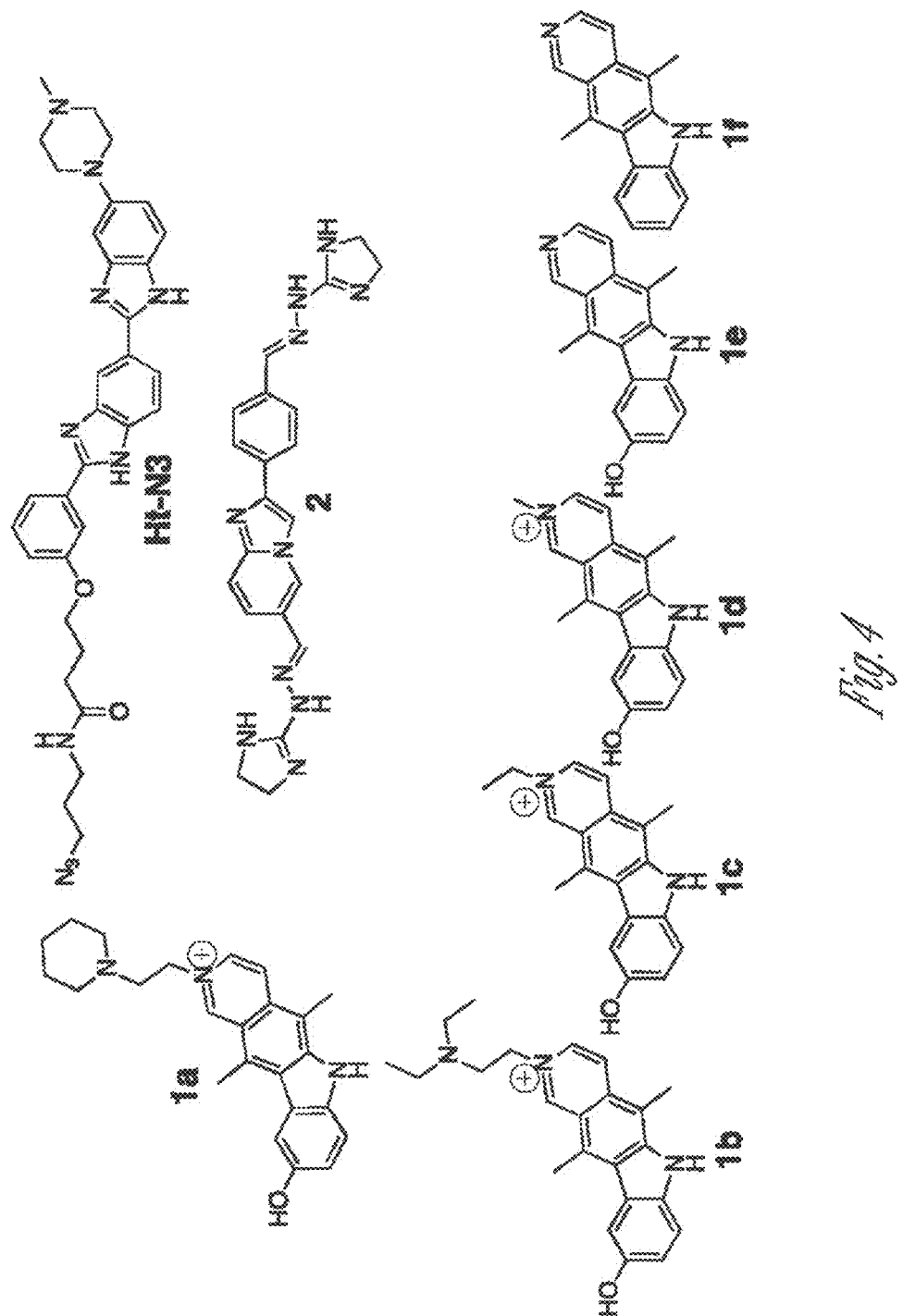
FIG. 4 shows the structures of the small molecules identified from an RNA-focused library that inhibit the $r(CGG)_{12}$-DGCR8Δ interaction and derivatives of the most potent monomeric compound (1a). 1b-1f were used to construct structure-activity relationships and define the active pharmacophore. Inhibition is markedly decreased for derivatives 1e and 1f (Table 1).

In order to assess the bioactivity of 1a, a model cellular system of FXTAS was used (8). Previously, it has been shown that pre-mRNA splicing defects are observed in survival of motor neuron 2 (SMN2) and B-cell lymphoma x (Bcl-x) mRNAs when cells express r(CGG)$^{exp}$ (8). These pre-mRNA splicing defects are due to sequestration of Sam68 by r(CGG)$^{exp}$; Sam68 directly regulates the alternative splicing of SMN2 and Bcl-x (a). Specifically, exon 7 of the SMN2 mRNA is included too frequently in FXTAS model systems; ~70% of SMN2 mRNA contains exon 7 when r(CGG)$^{exp}$ is expressed while exon 7 is included in only ~30% of SMN2 mRNA in cells that do not express r(CGG)$^{exp}$ (FIG. 4, top). Likewise, there are two isoforms of Bcl-x mRNA, Bcl-xL and Bcl-xS. In FXTAS cellular model systems, 60% of the Bcl-x mRNA is the Bcl-xL isoform. In healthy cells, only 40% of the mRNA is the Bcl-xL isoform (FIG. 4, bottom).

When cells that express r(CGG)$_{60}$ are treated with in, improvement in SMN2 and Bcl-x pre-mRNA splicing defects are observed (FIG. 4). For example, improvement of SMN2 splicing defects can be observed when cells are treated with as little as 20 μM of 1a. SMN2 mis-splicing is further improved at higher concentrations: treatment with 100 μM 1a improves pre-mRNA splicing levels to approximately 70% of wild type (absence of r(CGG)$^{exp}$) while treatment with 500 μM restores pre-mRNA splicing to levels wild type (FIG. 4). 1a also improves disregulation of Bcl-x splicing. Statistically significant improvement is observed when cells are treated with 100 μM of 1a while restoration of wild type splicing patterns are observed at 500 μM (FIG. 4). No statistically significant effect on SMN2 or Bcl-x splicing was observed when cells that do not express r(CGG)$_{60}$ are treated with 1a. This suggests that the improvement of pre-mRNA splicing defects is due to 1a displacing proteins from r(CGG)$_{60}$.

Control experiments were also completed to determine the specificity of 1a; that is if it affects the splicing of RNAs not controlled by Sam68. In these experiments, a PLEKHH2 (15) or cardiac troponin T (cTNT) (32) mini-gene was used, as their alternative splicing is not regulated by Sam68. The addition of 1a (500 μM) did not affect PLEKHH2 or cTNT alternative splicing (Figures S-4 & S-5). Thus, the effect of 1a on pre-mRNA splicing appears to be specific to the splicing of pre-mRNAs regulated by Sam68.

Figure 5A:
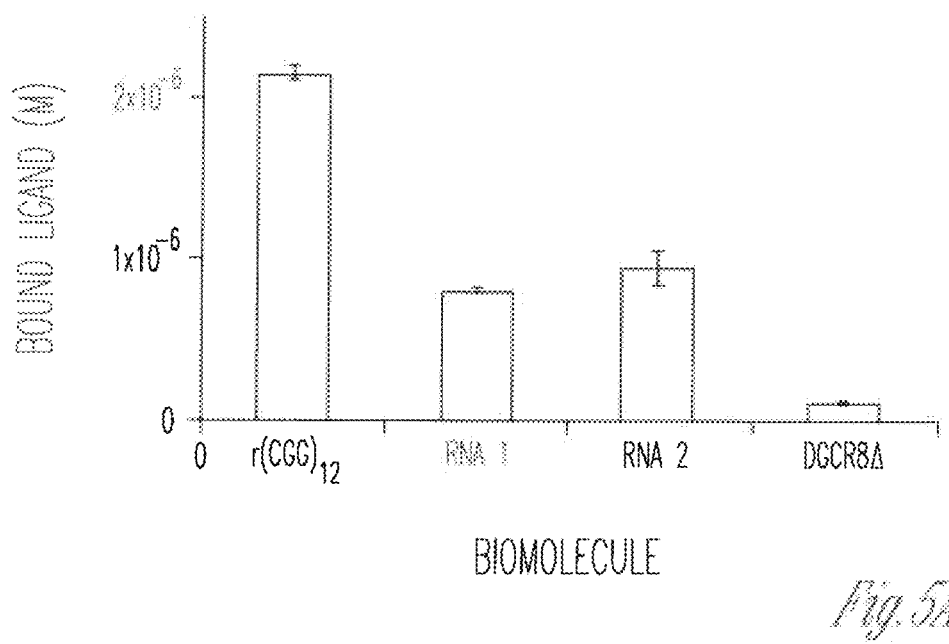
FIGS. 5A and 5B show: 5A: Results of competition dialysis experiments used to assess the specificity of 1a for $r(CGG)_{12}$; plot of the amount of ligand bound to various RNAs and DGCR8Δ; 5B: the secondary structures of two fully paired RNAs used in competition dialysis (SEQ ID NOs: 1 and 2).
Figure 5B:
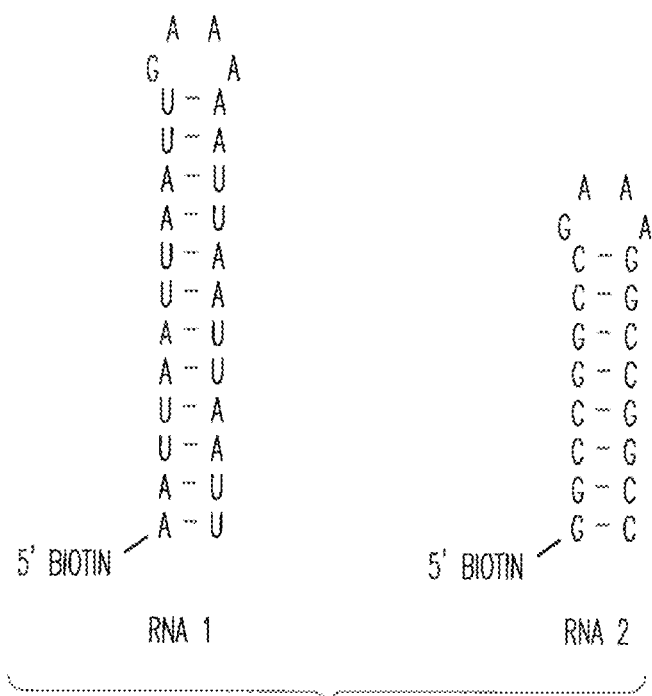
Figure 6A:
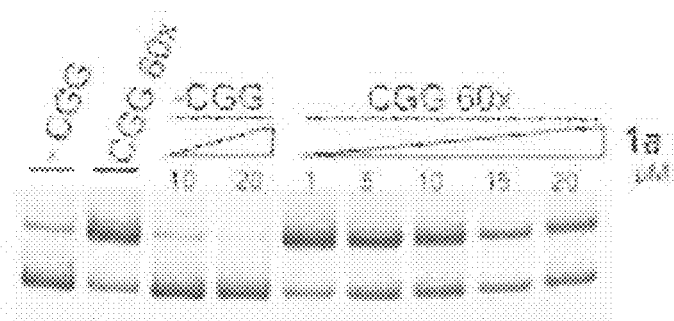
FIGS. 6A, 6B, and 6C show data indicating the in vivo efficacy of 1a against FXTAS as assessed by improvement in pre-mRNA splicing defects. Briefly, COS7 cells were transfected with an SMN2 or Bcl-x mini-gene in the presence or absence of a mini-gene that express 60 r(CGG) repeats (CGG 60X) FIG. 6A. The cells were then treated with 1a. Total RNA was harvested, and the alternative splicing of the SMN2 exon 7 or Bcl-x exon 2 was determined by RT-PCR.
Figure 6B:
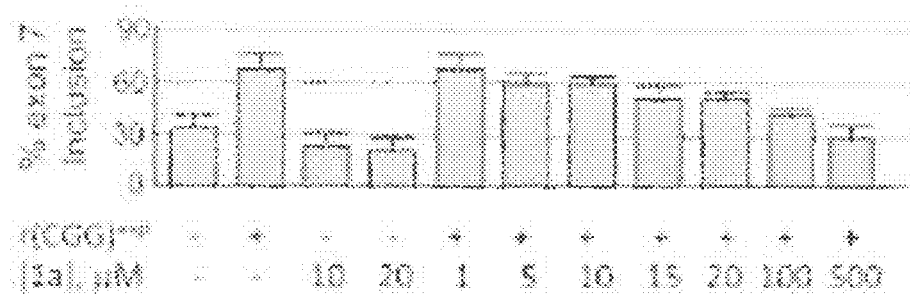
Figure 6C:
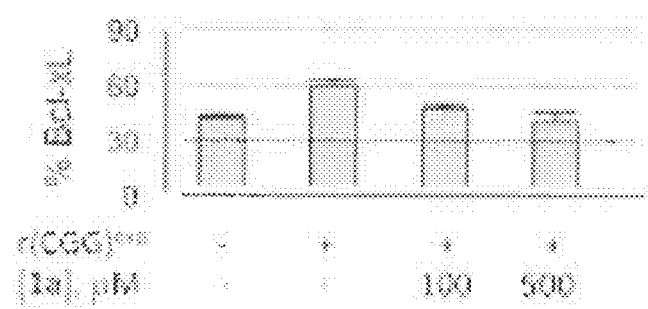
Figure 7A:
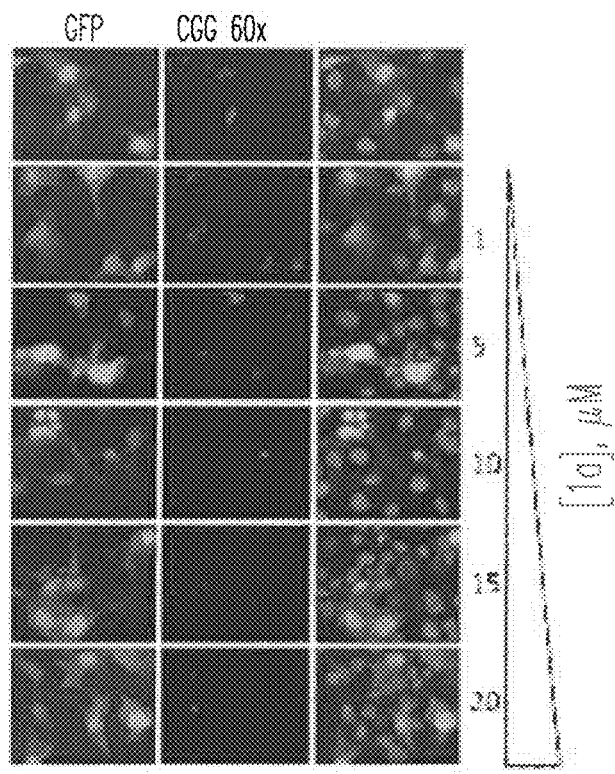
FIGS. 7A and 7B show data indicating that compound is decreases $r(CGG)^{exp}$-protein aggregates as assessed by fluorescence in situ hybridization (FISH). Briefly, COS7 cells were co-transfected with a plasmid encoding 60 r(CGG) repeats and a plasmid encoding GFP. Cells were then treated with 1a and probed with 5'(CCG)$_8$-Cy3 DNA oligonucleotide probe. Only cells that are GFP positive were analyzed for the presence of nuclear foci. Top.
Figure 7B:
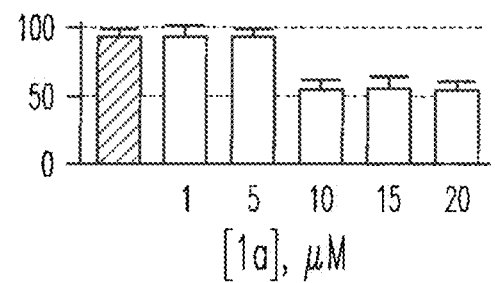

Another phenotype of cells expressing r(CGG)$^{exp}$ is the formation of nuclear foci. Additional studies were therefore completed by using a fluorescence in situ hybridization (FISH) assay to determine if 1a decreased the number or size of foci. As can be observed in FIG. 5, 1a reduces the size and the number of foci. Collectively, the improvement in the formation of foci and in the disregulation of pre-mRNA alternative splicing show that 1a binds r(CGG)$^{exp}$ in cellular systems and displaces bound proteins that are then free to complete their normal physiological functions.

Comparison to Other Small Molecules that Target RNA.

A few bioactive small molecules have been shown to bind to expanded triplet repeats in vivo and to improve associated defects (10-12, 15). For example, a bis-benzimidazole (11), pentamidine (15), and modularly assembled bis-benzimidazoles (12) target the r(CUG)$^{exp}$ that causes DM1. Each improves pre-mRNA splicing defects. In general, modularly assembled ligands that target multiple 5'CUG/3'GUC motifs in r(CUG)$^{exp}$ simultaneously are the more potent inhibitors. For example, a monomeric bis-benzimidazole (H1) improves pre-mRNA splicing defects in DM1 model systems to wild type levels when 2000 μM of compound is used. A dimeric modularly assembled compound that displays two copies of a bis-benzimidazole, 2H-4, improves pre-mRNA splicing levels back to wild type when cells are treated with a 50 μM solution of the compound. This represents a greater than 40-fold enhancement in bioactivity provided by a modular assembly approach even though the assembled compounds are of higher molecular weight and not classically "drug-like." The improved bioactivity of the modularly assembled compound could be due to the increased surface area occupied by the compound, residence time on the RNA target, and the affinity and selectivity of modularly assembled ligands for r(CUG)$^{exp}$ (12, 14).

In order to synthesize second-generation modularly assembled compounds that target r(CGG)$^{exp}$, a site that can be used to conjugate 1a-like compounds onto an assembly scaffold must be identified. Fortuitously, our SAR studies showed that the side chain that emerges from the pyridyl group can be altered since it does not affect potency. Thus, this site is ideal for the addition of reactive groups that can be anchored onto an assembly scaffold.

Implications.

The identification of a bioactive small molecule that targets r(CGG)$^{exp}$ not only provides lead compounds that could become therapies for FXTAS, but also other disorders that are mediated by r(CGG)$^{exp}$. Notably, this includes Fragile X Syndrome (FXS), an incurable disease that is the most common single gene cause of autism (33). In this case, FXS is thought to be caused by RNAi-based mechanism in which r(CGG)$^{exp}$ is cleaved into small RNAs that enable transcriptional silencing (7). Thus, if it is indeed possible to reactivate this locus chemically, then a small molecule that targets r(CGG)$^{exp}$, and inhibits processing into smaller RNAs could activate the FMR1 locus.

Lastly, the ability of a small molecule to target r(CGG)$^{exp}$ in cellular models of FXTAS and reverse a pre-mRNA splicing defect provides further evidence for an RNA gain-of-function mechanism. Since this study is another example of a small molecule that targets a non-ribosomal RNA that causes disease, it provides further evidence that small molecules can be developed to target non-coding regions in RNA even though these targets have been thought to be recalcitrant to small molecule intervention.

Accordingly, the invention provides, in various embodiments, a compound of formula (I)

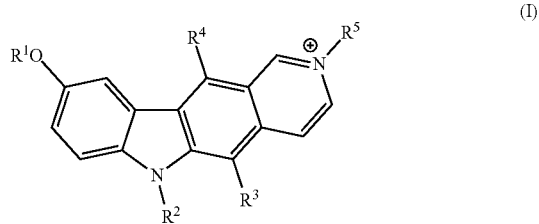

(I)

wherein
$R^1$ is H, (C1-C6)alkyl, or (C1-C6)alkanoyl;
$R^2$ is H, (C1-C6)alkyl, or (C1-C6)alkanoyl;
$R^3$ and $R^4$ are independently H, (C1-C6)alkyl, (C1-C6)haloalkyl, (C1-C6)alkoxyalkyl (C1-C6)haloalkoxyalkyl, or (C6-C10)aryl;
$R^5$ is (C1-C6)alkyl, (C1-C6)alkoxy(C1-C6)alkyl, (C1-C6)haloalkyl, (C1-C6)haloalkoxy, aryl(C1-C6)alkyl, heterocyclyl(C1-C6)alkyl, heteroaryl(C1-C6)alkyl, or $(R^6)_2$N—(C1-C6)alkyl, wherein $R^6$ is H or (C1-C6)alkyl;
wherein any alkyl, alkanoyl, alkoxy, aryl, heterocyclyl, or heteroaryl can be substituted with 0-3 J groups, wherein J is any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, $R_2N$, $R_2NC(O)$, $R_2NC(O)O$, $R_2NC(O)NR$, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl;

R is independently at each occurrence H, (C1-C6)alkyl, or (C6-C10)aryl, wherein any alkyl or aryl group is substituted with 0-3 J;

provided the compound of formula (I) is not any of

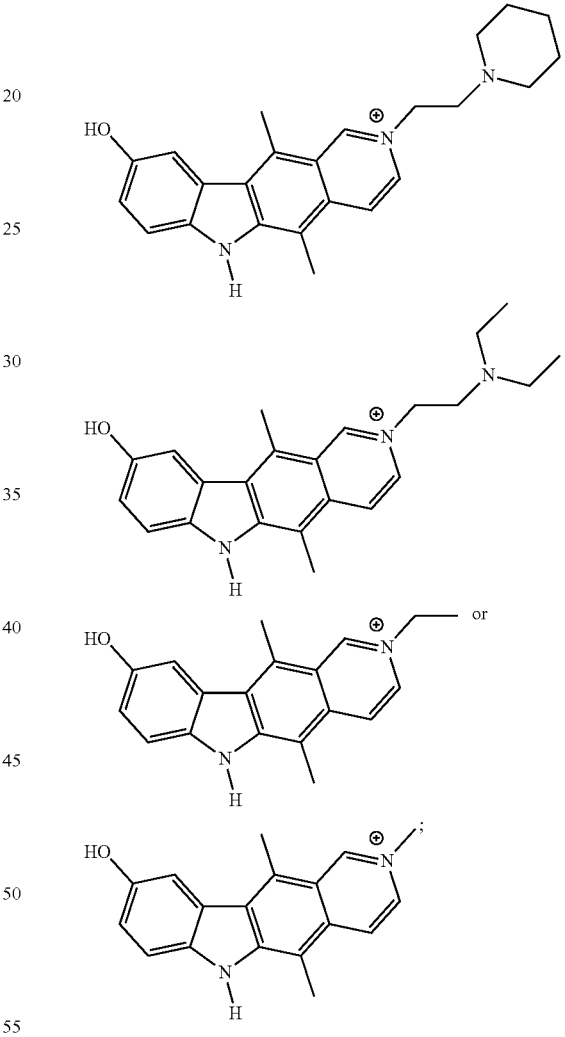

or a pharmaceutically acceptable salt thereof.

For example, R can be H, or $R^2$ can be H, or both can be H.

For example, $R^3$ and $R^4$ can each be methyl.

For example, for formula (I) $R^5$ can be $(R^6)_2$N—(C1-C6)alkyl, wherein $R^6$ is H or (C1-C6)alkyl; or $R^5$ can be (C1-C6)alkyl; or $R^5$ can be a triazolylalkyl group, wherein the triazolyl group can be unsubstituted or can be substituted with 1-3 J groups.

For example, the compound can be an analog of 9-hydroxyellipticine comprising an N-alkylated pyridinium moiety: formula (I) below illustrates what is meant by an N-alkylated pyridium moiety, that is, the pyridine ring of the ellipticine is quaternarized by alkylation with a group, shown as $R^5$ below, such that the molecule bears a permanent positive charge. For charge balance, a suitable anion is present, e.g., halide, sulfate, phosphonate, alkylsulfonate, etc., in the appropriate stoichiometric ratio.

In various embodiments, the invention provides a dimeric r(CGG) binding compound that can improve the pre-mRNA defects in FXTAS cellular model systems. The dimeric compounds, which comprise two 9-hydroxyellipticine analogous moieties, can be a dimeric r(CGG) binding compound of formula (II)

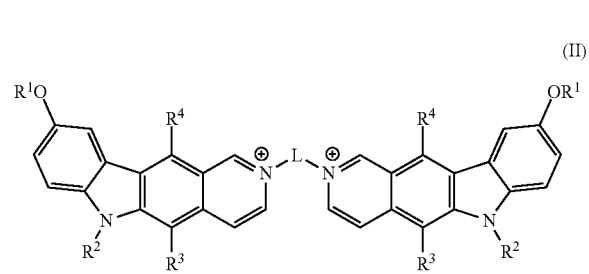

wherein $R^1$, $R^2$, $R^3$, and $R^4$ are as defined for the monomeric compound of formula (I), and wherein L is a linker comprising a polypeptide backbone bonded by two respective nitrogen atoms thereof to a nitrogen atom of a respective 1, 2, 3-triazole group via a respective (C1-C6)alkylene group optionally further comprising a glycyl residue, each respective triazole group being bonded via a (C1-C6)alkylene group to the respective pyridinium nitrogen atom of each ellipticine scaffold; or a pharmaceutically acceptable salt thereof; or a pharmaceutically acceptable salt thereof.

In various embodiments, the dimeric r(CGG) binding compound of formula (II) can comprise a linker L of formula (LI)

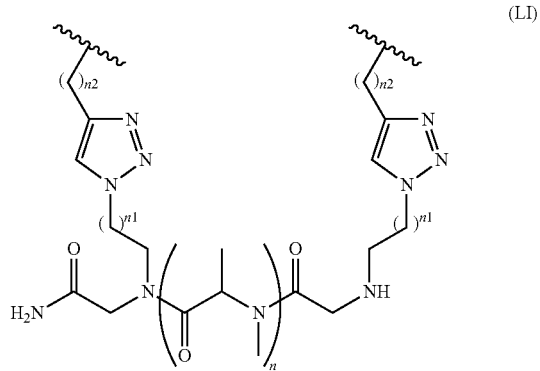

wherein n=1, 2, 3, 4, 5, 6, 7, or 8; each independently selected n1=0, 1, 2, 3, 4, or 5; and each independently selected n2=1, 2, 3, 4, 5, or 6; and wherein a wavy line indicates a position of bonding to the respective pyridinium nitrogen atom of formula (II).

As the term is used herein, an "ellipticine scaffold" refers to the tetracyclic ring system substituted with groups $R^1$-$R^4$. A "linker" joins the two ellipticine scaffolds to form the dimeric r(CGG) binding compound of formula (II). The compound of formula (II) can comprise a linker L of formula LI, wherein the two wavy lines indicate points of bonding to the two pyridinium nitrogen atoms of the two respective ellipticine scaffolds.

In various embodiments, the invention provides a method of inhibiting a messenger RNA molecule with an repeat r(CGG) sequence, such as an expanded r(CGG) sequence (a r(CGG)$^{exp}$ sequence) from binding to a protein with a binding affinity for a RNA hairpin loop comprising a non-Watson-Crick G-O nucleotide pair, comprising contacting the messenger RNA molecule having the repeat r(CGG) sequence, e.g., a r(CGG)$^{exp}$ sequence, and an effective amount or concentration of a compound of formula (I)

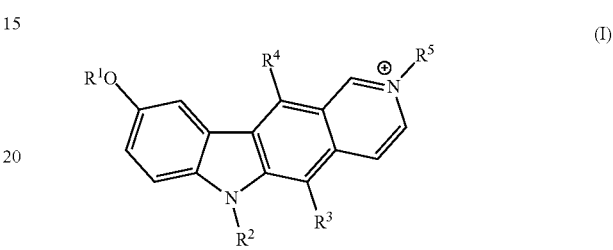

wherein
$R^1$ is H, (C1-C6)alkyl, or (C1-C6)alkanoyl;
$R^2$ is H, (C1-C6)alkyl, or (C1-C6)alkanoyl;
$R^3$ and $R^4$ are independently H, (C1-C6)alkyl, (C1-C6)haloalkyl, (C1-C6)alkoxyalkyl (C1-C6)haloalkoxyalkyl, or (C6-C10)aryl;
$R^5$ is (C1-C6)alkyl, (C1-C6)alkoxy(C1-C6)alkyl, (C1-C6)haloalkyl, (C1-C6)haloalkoxy, aryl(C1-C6)alkyl, heterocyclyl(C1-C6)alkyl, heteroaryl(C1-C6)alkyl, or $(R^6)_2N$—(C1-C6)alkyl, wherein $R^1$ is H or (C1-C6)alkyl;
wherein any alkyl, alkanoyl, alkoxy, aryl, heterocyclyl, or heteroaryl can be substituted with 0-3 J groups, wherein J is any of halo, (C1-C6)alkyl, (C1-C6)alkoxy, (C1-C6)haloalkyl, hydroxy(C1-C6)alkyl), alkoxy(C1-C6)alkyl, (C1-C6)alkanoyl, (C1-C6)alkanoyloxy, cyano, nitro, azido, $R_2N$, $R_2NC(O)$, $R_2NC(O)O$, $R_2NC(O)NR$, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy (C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl:
R is independently at each occurrence H, (C1-C6)alkyl, or (C6-C10)aryl, wherein any alkyl or aryl group is substituted with 0-3 J; or,
an effective amount or concentration of a dimeric r(CGG) binding compound of formula (II)

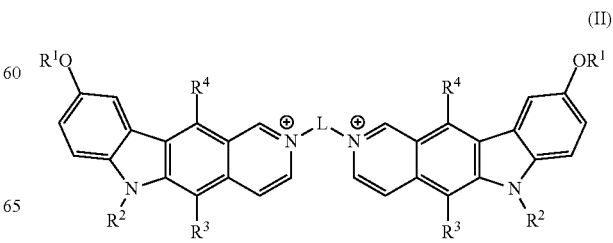

wherein R¹, R², R³, and R⁴ are as defined for the monomeric compound of formula (I), and wherein L is a linker comprising a polypeptide backbone bonded by two respective nitrogen atoms thereof to a nitrogen atom of a respective 1,2,3-triazole group via a respective (C1-C6)alkylene group optionally further comprising a glycyl residue, each respective triazole group being bonded via a (C1-C6)alkylene group to the respective pyridinium nitrogen atom of each ellipticine scaffold; or a pharmaceutically acceptable salt thereof; or a pharmaceutically acceptable salt thereof;

or a pharmaceutically acceptable salt thereof.

For example, $R^1$ can be H, or $R^2$ can be H, or both.

For example, $R^3$ and $R^4$ can each be methyl.

For example, for formula (I) $R^3$ can be $(R^6)_2N$—(C1-C6)alkyl, wherein $R^6$ is H or (C1-C6)alkyl, or $R^5$ can be (C1-C6)alkyl; or $R^5$ can be a triazolylalkyl group, wherein the triazolyl group can be unsubstituted or can be substituted with 1-3 J groups.

More specifically, for practice of the inventive method, the compound of formula (I) can be any of:

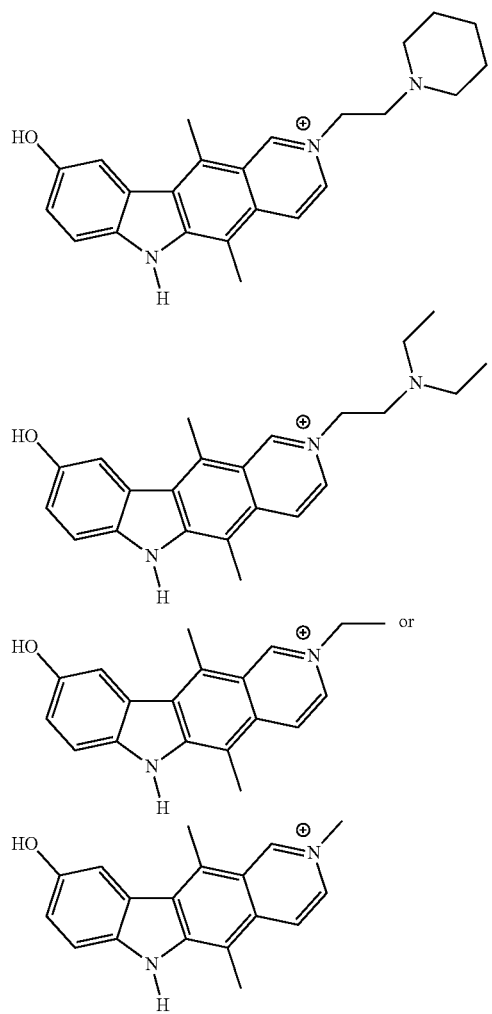

or a pharmaceutically acceptable salt thereof.

In various embodiments of the method, the dimeric r(CGG) binding compound of formula (II) can comprise a linker of formula (LI)

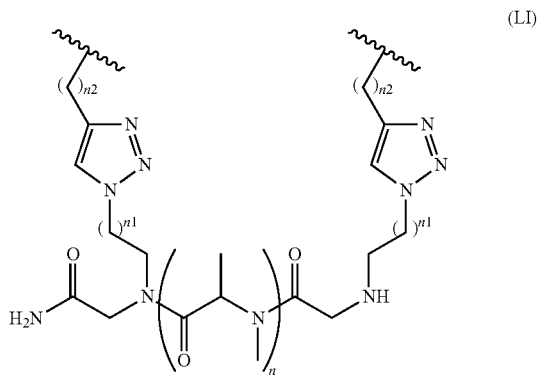

(LI)

wherein n=1, 2, 3, 4, 5, 6, 7, or 8; each independently selected n1=0, 1, 2, 3, 4, or 5; and each independently selected n2=1, 2, 3, 4, 5, or 6; and wherein a wavy line indicates a position of bonding to the respective pyridinium nitrogen atom of formula (II).

For example, the contacting can be in vivo in a patient wherein the inhibiting is medically indicated for treatment of a condition, e.g, wherein the patient is suffering from Fragile X-associated Tremor Ataxia Syndrome.

In various embodiments, the invention can provide a method of inhibiting a messenger RNA molecule with a repeat r(CGG) sequence, e.g., an expanded r(CGG) sequence (r(CGG)$^{exp}$), from binding to a protein with a binding affinity for a RNA hairpin loop comprising a non-Watson-Crick G-G nucleotide pair, comprising contacting the messenger RNA molecule having the repeat r(CGG) sequence and an effective amount or concentration of 9-hydroxyellipticine bearing an N-substituted pyridinium moiety, or an analog thereof.

The invention provides, in various embodiments, a method of treatment of Fragile X-associated Tremor Ataxia Syndrome, comprising administering to a patient afflicted therewith a therapeutically effective dose of a compound of formula (I)

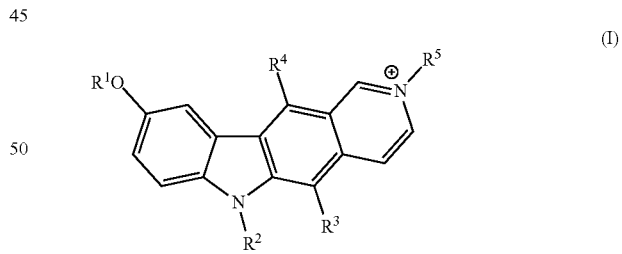

(I)

wherein $R^1$ is H, (C1-C6)alkyl, or (C1-C6)alkanoyl;

$R^2$ is H, (C1-C6)alkyl, or (C1-C6)alkanoyl;

$R^3$ and $R^4$ are independently H, (C1-C6)alkyl, (C1-C6)haloalkyl, (C1-C6)alkoxyalkyl (C1-C6)haloalkoxyalkyl, or (C6-C10)aryl;

$R^5$ is (C1-C6)alkyl, (C1-C6)alkoxy(C1-C6)alkyl, (C1-C6)haloalkyl, (C1-C6)haloalkoxy, aryl(C1-C6)alkyl, heterocyclyl(C1-C6)alkyl, heteroaryl(C1-C6)alkyl, or $(R^6)_2N$—(C1-C6)alkyl, wherein $R^1$ is H or (C1-C6)alkyl;

wherein any alkyl, alkanoyl, alkoxy, aryl, heterocyclyl, or heteroaryl can be substituted with 0-3 J groups, wherein J is any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, R$_2$N, R$_2$NC(O). R$_2$NC(O)O, R$_2$NC(O)NR, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl;

R is independently at each occurrence H, (C1-C6)alkyl, or (C6-C10)aryl, wherein any alkyl or aryl group is substituted with 0-3 J; or, an effective amount or concentration of a dimeric r(CGG) binding compound of formula (II)

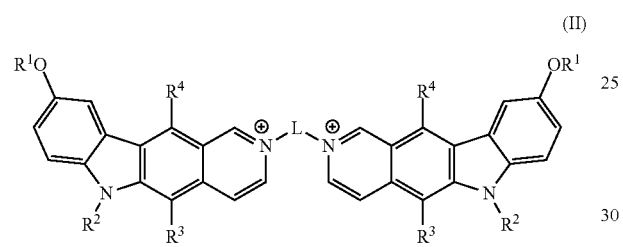

(II)

wherein R$^1$, R$^2$, R$^3$, and R$^4$ are as defined for the monomeric compound of formula (I), and wherein L is a linker comprising a polypeptide backbone bonded by two respective nitrogen atoms thereof to a nitrogen atom of a respective 1,2,3-triazole group via a respective (C1-C6)alkylene group optionally further comprising a glycyl residue, each respective triazole group being bonded via a (C1-C6)alkylene group to the respective pyridinium nitrogen atom of each ellipticine scaffold; or a pharmaceutically acceptable salt thereof.

For example, R$^1$ can be H, or R$^2$ can be H, or both.

For example, R$^3$ and R$^5$ can each be methyl.

For example, for formula (I) R$^5$ can be (R$^6$)$_2$N—(C1-C6)alkyl, wherein R$^6$ is H or (C1-C6)alkyl, or R$^5$ can be (C1-C6)alkyl; or R$^5$ can be a triazolylalkyl group, wherein the triazolyl group can be unsubstituted or can be substituted with 1-3 J groups.

More specifically, for practice of the inventive method, the compound of formula (I) can be any of:

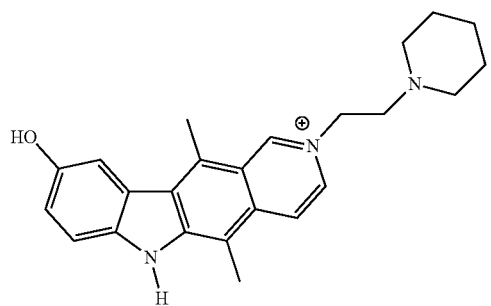

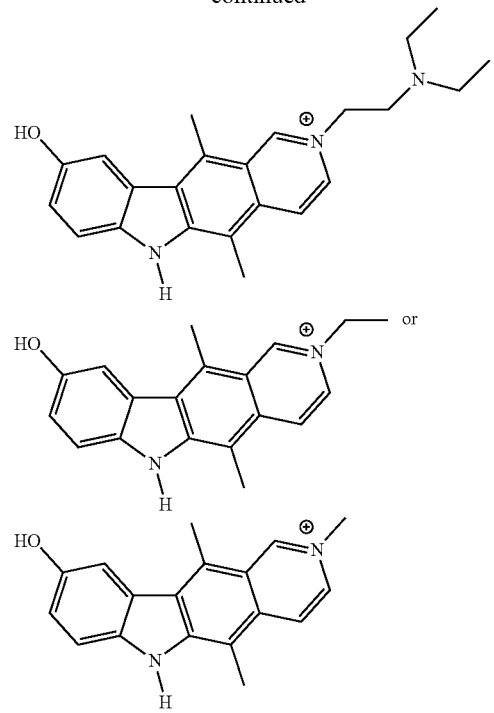

or a pharmaceutically acceptable salt thereof.

In various embodiments of the method, the dimeric r(CGG) binding compound of formula (II) can comprise a linker of formula (LI)

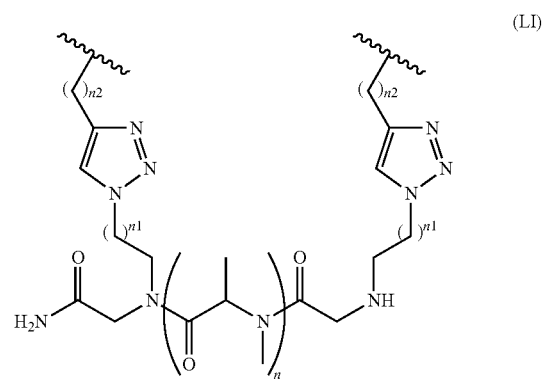

(LI)

wherein n=1, 2, 3, 4, 5, 6, 7, or 8; each independently selected n1=0, 1, 2, 3, 4, or 5; and each independently selected n2=1, 2, 3, 4, 5, or 6; and wherein a wavy line indicates a position of bonding to the respective pyridinium nitrogen atom of formula (II).

In various embodiments, the invention can provide a method of treatment of Fragile X-associated Tremor Ataxia Syndrome, comprising administering to a patient afflicted therein, an N-substituted pyridinium moiety, or an analog thereof.

Table 1, below, provides specific data for compounds 1a-1f (see FIG. 4) concerning the potency of the respective compound for disruption of the r(CGG)$_{12}$-DGCR8Δ complex, expressed as percentage displacement at 25 µM, IC$_{50}$ (µM) and Kd (nM). The higher the percentage displacement at the fixed concentration of the compound, the more potent the compound is. Compounds 1a-1d were the most potent of the tested compounds.

TABLE 1

The potencies of 1a-1f for disruption of the r(CGG)$_{12}$-DGCR8Δ complex and the corresponding affinities for an RNA containing one 5'CGG/3'GGC motif. The potencies of the compounds are reported as IC$_{50}$s as determined from the TR-FRET assay.

|  | 1a | 1b | 1c | 1d | 1e | 1f |
|---|---|---|---|---|---|---|
| Percentage displacement at 25 μM | 85 ± 1 | 91 ± 5 | 96 ± 9 | 87 ± 5 | 46 ± 5 | 0 |
| IC$_{50}$, μM | 13 ± 0.4 | 8 ± 0.3 | 13 ± 0.2 | 7 ± 0.2 | ~25 | ND[a] |
| K$_d$, nM | 76 ± 4 | 38 ± 1 | 69 ± 5 | 50 ± 18 | NM[b] | NM[b] |

[a]ND denotes that no determination could be made.
[b]NM denotes that no measurement was made.

Structure-activity analysis of the monomeric compounds indicated portions of the 9-hydroxyellipticine analog structure necessary to preserve for RNA sequence binding activity, and portions that could be modified into a dimeric compound without loss of activity. For example, the oxygen atom on the ellipticine 9-position should be conserved for bioactivity; thus the group designated OR$^1$ in formula (I) and in formula (II) should be OH or an O-alkyl or O-acyl group. Enhanced bioactivity is observed when the quaternary, positively-charged pyridinium group at the opposite end of the ellipticine skeleton is also preserved. However, the structure of the group designated R$^5$ in formula (I), i.e., the group bonded to the quaternary pyridinium nitrogen atom, is not highly related to bioactivity. Accordingly, the inventors herein designed a dimeric structure, formula (I), based on these data.

For example, the invention can provide a compound of formula (U) having as linker L a group of formula (LI), the compound being of formula 2E-nNME

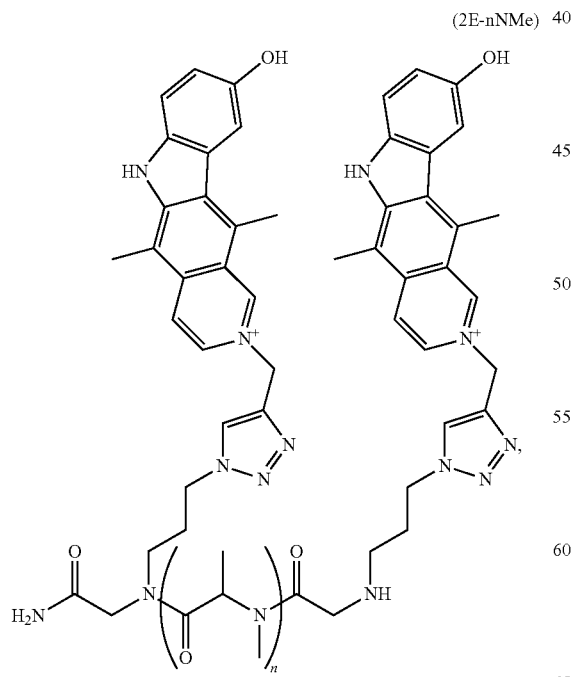

(2E-nNMe)

with varying numbers of repeat units n for the N-methylalanine oligomeric unit ranging from 1 to about 10 (e.g., whole numbers 1-6, 1-8, or 1-10), which is reflected in the nomenclature used herein. For instance, when n=1, the compound of formula 2E-nNMe is termed 2E-1NMe, and so forth.

Table 2 presents data indicating the potencies of compound 2E-1 NMe through 2E-6NMe, i.e., compounds of the above structure with the number of the N-methylalanine repeating group varying from 1 to 6.

In various embodiments, the invention provides modularly assembled small molecules targeting r(CGG)$^{exp}$ that improve the pre-mRNA defects in FXTAS cellular model systems. Modularly assembled compounds display two copies of an hydroxyl ellipticine-like module that was previously shown to bind r(CGG)$^{exp}$.

The optimal dimeric compounds improve pre-mRNA splicing with 10-fold higher potency than the monomer, e.g., a compound of formula 1a:

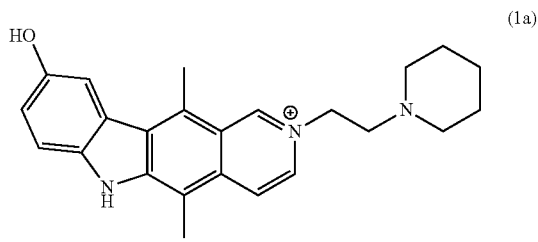 [SMILES: Cc1c2cc[n+](CCN3CCCCC3)cc2c(C)c2c1[nH]c1ccc(O)cc12]

(1a)

compared to a comparable dimeric compound of formula (II) wherein two ellipticine scaffolds are joined by linker L, e.g., joined by linker (LI).

TABLE 2

Potencies of compounds in inhibition of r(CGG)12-DGCR8Δ complex

| | r(CGG)$_{12}$-DGCR8Δ complex formation, % | | |
|---|---|---|---|
| | 1 μM | 10 μM | IC$_{50}$, μM |
| 2E-1NMe | 78.0 ± 1.2 | 25.3 ± 2.0 | — |
| 2E-2NMe | 74.3 ± 2.6 | 33.0 ± 1.8 | — |
| 2E-3NMe | 83.4 ± 0.8 | 17.8 ± 2.1 | — |
| 2E-4NMe | 75.6 ± 1.9 | 18.8 ± 3.7 | — |
| 2E-5NMe | 39.6 ± 0.6 | 5.0 ± 2.6 | 0.47 ± 0.08 (3.52 ± 0.61)[a] |
| 2E-6NMe | 72.0 ± 0.8 | 9.2 ± 1.5 | — |
| 1a | 66.9 ± 0.7 | 20.4 ± 0.8 | 3.84 ± 0.30 (20.1 ± 1.2)[a] |

[a]Value in parenthesis is IC$_{50}$ at the presence of 62 times of competitor, tRNA Therefore, developing small molecules targeting r(CGG) exp can be a strategy for inhibition of the pathogenic mechanism, protein sequestration, because small molecules binding to r(CGG)exp can release the sequestrated proteins (FIG. 2). However, although attention has been paid to targeting RNA for curing RNA-based diseases and considerable effort has been made to identify small molecules that can interact with RNA, it is challenging to develop bioactive small molecules because of a poor understanding of RNA recognition principles. Previously, we identified hydroxyellipticine derivatives, such as 1a, as compounds that can displace proteins from r(CGG)$^{exp}$ with low micromolar IC$_{50}$s and bind to r(CGG)$^{exp}$ with nanomolar K$_d$s (FIG. 4 and Table 1). In FXTAS models, the reduced formation of r(CGG)$^{exp}$ aggregation in the presence of 1a indicates that 1a targets r(CGG)$^{exp}$ in cell culture and displaces proteins that bind to r(CGG)$^{exp}$. Further evidence of inhibition of the protein-r(CGG)$^{exp}$ complex in cells is the observed improvement of pre-mRNA splicing defects by 1a. Thus, 1a displaces protein from r(CGG)$^{exp}$, allowing these proteins to control pro-mRNA splicing.

Modular assembly approach is a powerful method to optimize bioactivity (both binding affinity and selectivity) of small molecules targeting the repeats. To better understand binding of 1a to r(CGG)$^{exp}$, a structure-activity relationship analysis was completed. These studies are summarized herein, and provide an attachment point to construct improved compounds targeting r(CGG)$^{exp}$ by using a modular assembly strategy to provide the dimeric compounds of formula (II) having greater potency at binding r(CGG) sequences.

Figure 13A:
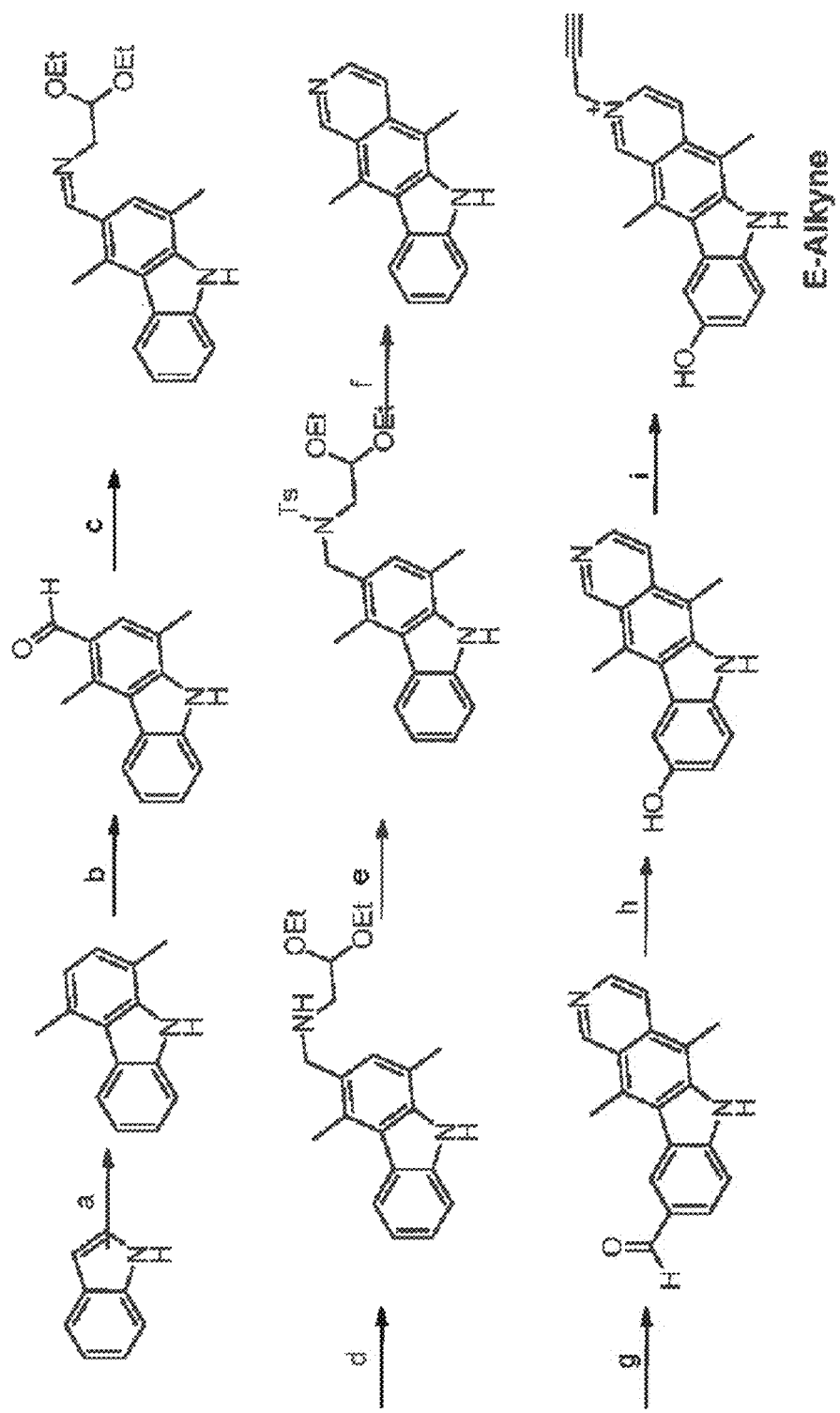
Figure 13B:
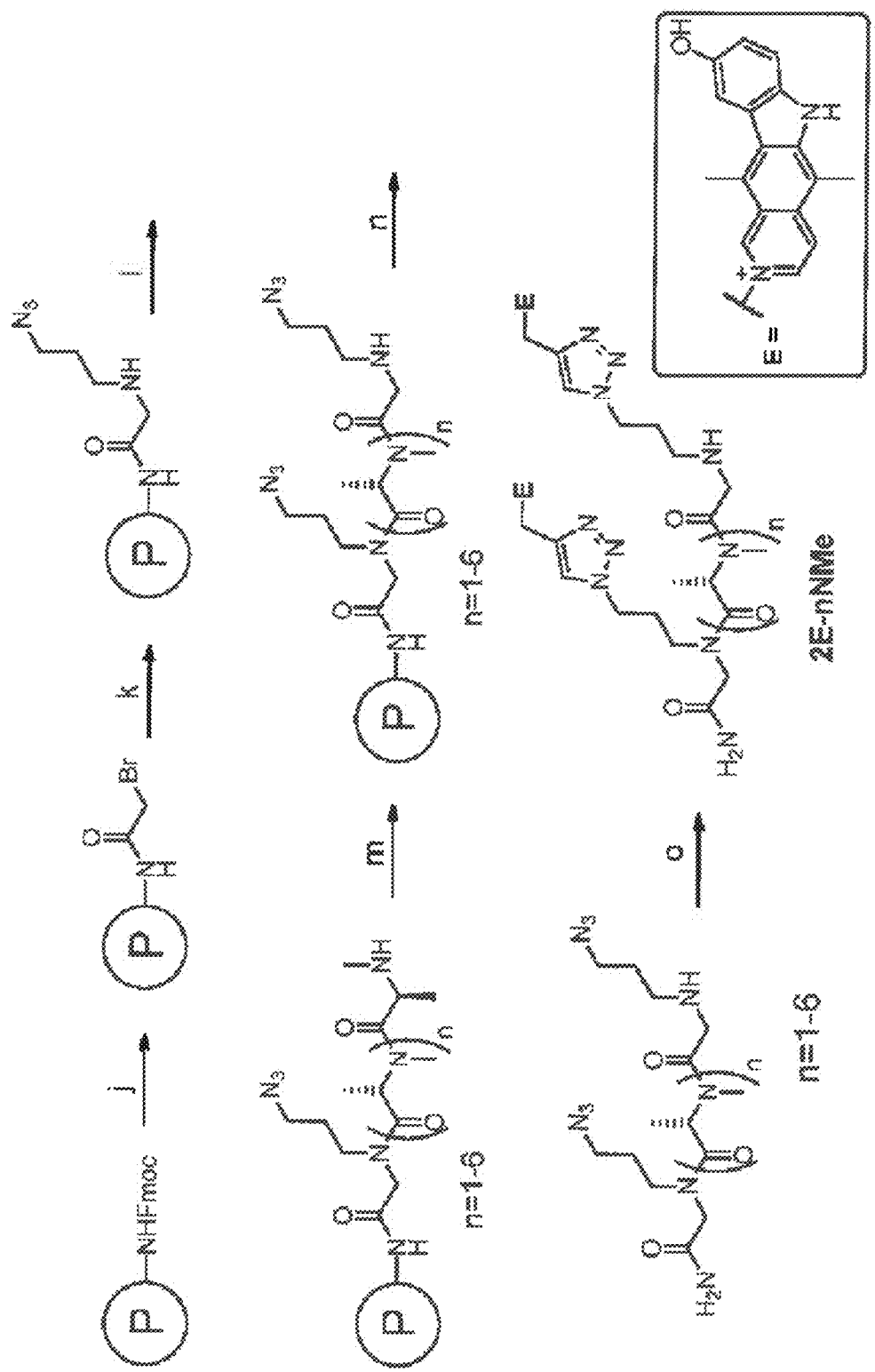

Synthesis of a r(CGG)$^{exp}$-Binding Compound (Module) Suitable for Modular Assembly.

r(CGG)$^{exp}$ folds into a hairpin that displays multiple copies of 5'C<u>G</u>G/3'G<u>GC</u> motifs. Thus, by displaying a small molecule that binds this repeating motif multiple times on the same backbone, high affinity, and selective compounds can be designed to target r(CGG)$^{exp}$. We previously identified that 1a binds 5'C<u>G</u>G/3'G<u>GC</u> motifs and improves r(CGG)$^{exp}$-associated defects in cellular models. We therefore synthesized a derivative that contains an alkyne functional group (9-hydroxy-N-propargylellipticine; E-alkyne; FIG. 13A), such that it can be conjugated to an azide-functionalized polymeric (N-methyl peptide) backbone (FIG. 13B).

The scheme for the synthesis of E-alkyne is shown in FIG. 13. Ellipticine was synthesized from indole via six reaction steps as reported herein, followed by formylation and Baeyer-Villiger oxidation reaction to obtain 9-hydroxyellipticine. The reaction of 9-hydroxyellipticine with propargyl bromide yielded the desired module compound containing a reactive ethynyl group, termed, E-alkyne.

Synthesis of N-Methylalanine Peptide Backbone and Modularly Assembled Small Molecules Targeting r(CGG)$^{exp}$.

In order to display multiple E-alkyne modules on a polymeric backbone, a N-methyl peptide scaffold was employed. Their synthesis is modular in nature, allowing for precise control of the valency of the r(CGG)$^{exp}$-binding modules and the distance between them. That is, the synthesis of PTAs is iterative: 3-azidopropylamine is coupled to the growing PTA backbone (used to couple E-alkyne; controls valency) followed by N-methyl-L-alanine (from 1-6 couplings; controls the distance between azides) and then 3-azidopropylamine (FIG. 13B). (This process can be repeated to afford compounds with higher valencies such as trimers, tetramers, etc.) Following the synthesis of the PTA backbone, E-alkyne is coupled via a Cu-catalyzed click reaction (FIG. 13B). Another advantage of PTAs is that they are more rigid than other scaffolds such as peptoids, potentially pre-organizing the RNA-binding module for binding r(CGG)$^{exp}$. A library of dimeric compounds (displaying two E-alkyne modules: 2E-nNMe where n denotes the number of spacing modules) was synthesized by using this approach. After peptide cleavage from Rink amide resin and HPLC purification, the PTAs were conjugated with E-alkyne and then purified to homogeneity by HPLC.

Screening Dimeric Compounds for Inhibition of r(CGG)$^{exp}$-DGCR8 Complex

We therefore employed a previously described time-resolved fluorescence resonance energy transfer (TR-FRET) assay to determine if dimeric compounds can inhibit formation of a r(CGG)$_{12}$-DGCR8D complex and which is the most potent. We screened the library of dimers, 2E-1NMe-2E4NMe at both 1 mM and 10 mM (Table 2). At both concentrations, 2E-5NMe (a dimer with five N-methyl-L-alanine spacers separating E binding modules) is the most potent compound: at 1 mM, 60% of the r(CGG)$_{12}$-DGCR8D complex was inhibited while at 10 mM, 95% of the complex is inhibited. 2E-5NMe has IC$_{50}$ of 0.47 mM (Table 2) and is ~8-fold more potent than the monomer, 1a (Table 1).

Improvement of Pre-mRNA Splicing Defects.

Figure 14:
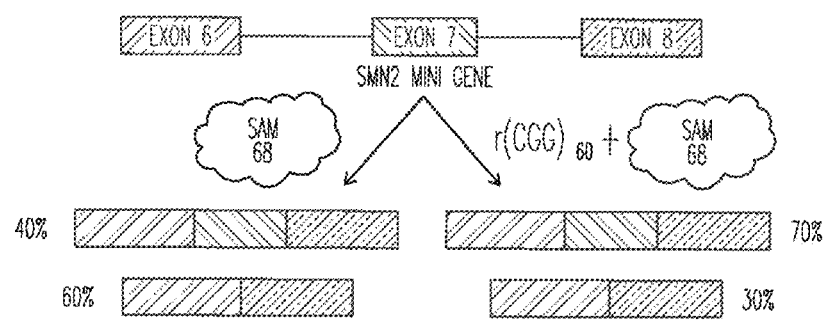
FIG. 14 shows a schematic of the alternative pre-mRNA splicing of SMN2 minigene.
Figure 15A:
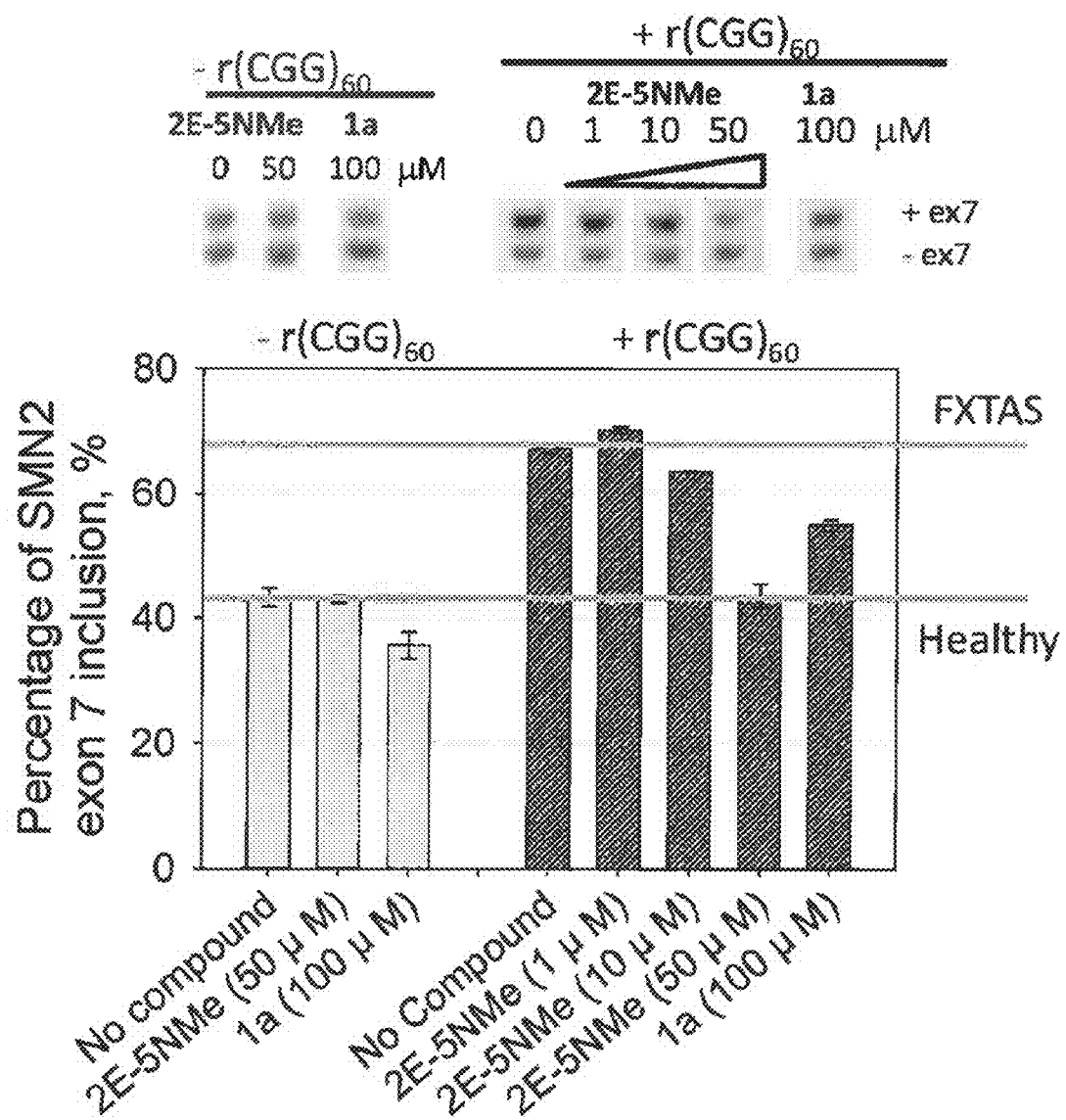
FIGS. 15A, 15B, and 15C shows evidence showing reduction of pro-mRNA splicing defects by compound 2E-5NMe. Briefly, COS7 cells were co-transfected with plasmids expressing an SMN2 alternative splicing reporter and $r(CGG)_{60}$. The transfection cocktail was removed, and the cells were incubated with fresh medium containing serially diluted concentrations of compound for 24 h.
Figure 15B:
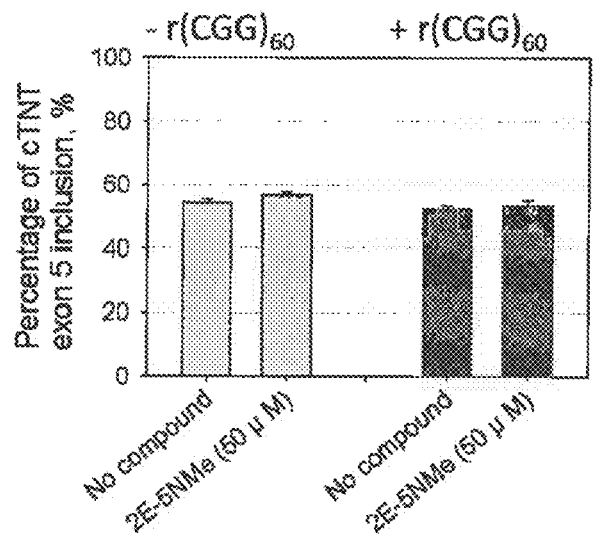
Figure 15C:
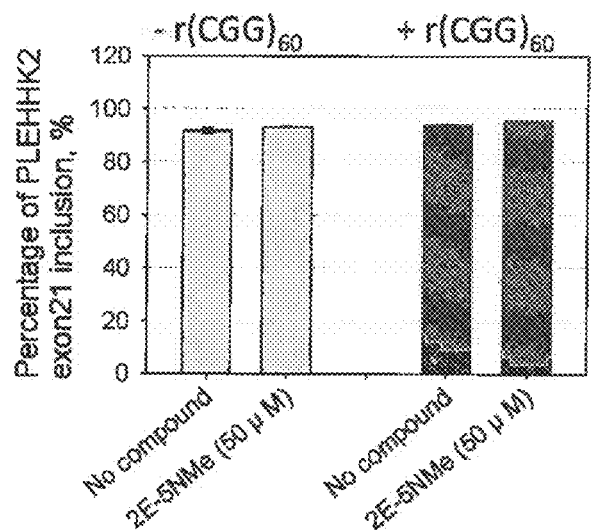

Encouraged by our TR-FRET assay results, we tested the bioactivity of the optimal dimeric small molecule, 2E-5NMe, by using a FXTAS cellular model. In the FXTAS cell model, r(CGG)$^{exp}$ binds and sequesters Sam68, a pre-mRNA splicing regulator. Sequestration of Sam68 causes its inactivation and dysregulation of alternative pre-mRNA splicing. In particular, the alternative splicing of exon 7 of the survival motor neuron-2 pre-mRNA (SMN2; involved in maintenance of motor neurons and mRNA processing) is dysregulated. Exon 7 is included too frequently when r(CGG)$^{exp}$ is expressed, ~70% of time as compared to normal cells in which exon 7 has an inclusion rate of only ~40% (FIG. 14). Experiments were completed as previously described. Briefly. COS7 cells were co-transfected with plasmids expressing an SMN2 alternative splicing reporter and r(CGG)$_{60}$. The transfection cocktail was removed, and the cells were incubated with fresh medium containing serially diluted concentrations of compound for 24 h. See FIG. 15A. Total RNA was harvested, and splicing patterns were analyzed via RT-PCR. Remarkably, at 50 mM concentration, 2E-5NMe restores alternative pre-mRNA splicing patterns back to the wild type. The monomer 1a required 10 times higher concentration for the same effect. Importantly, 2E-5NMe does not affect alternative splicing in healthy cells or the alternative splicing of pre-mRNAs not regulated by Sam68 (cardiac troponin T (cTNT) FIG. 15B, and pleckstrin homology domain containing, family H (with MyTH4 domain) member 2 (PLEKHH2), FIG. 15C). These results suggest that the improvement of the SMN2 pre-mRNA splicing is due to 2E-5NMe binding r(CGG)$_{60}$ and displacing proteins from it.

EXAMPLES

Oligonucleotide Preparation and Purification.

The RNAs used in the protein displacement assay (5'-biotin-(CGG)$_{12}$; SEQ ID NO:4) and competition dialysis were purchased from Dharmacon. The ACE protecting groups were cleaved using Dharmacon's deprotection buffer (100 mM acetic acid, adjusted to pH 3.8 with TEMED) by incubating at 60° C. for 2 h. The samples were lyophilized, resuspended in water, and desalted using a PD-10 gel filtration column (GE Healthcare). The concentrations were determined by absorbance at 90° C. using a Beckman Coulter DU800 UV-Vis spectrophotometer equipped with a Peltier temperature controller unit. Extinction coefficients (at 260 nm) were calculated using the HyTher server (34, 35), which uses nearest neighbors parameters (36).

DGCR8Δ Expression and Purification.

His-tagged DGCR8Δ was expressed in *Escherichia coli* BL21 cells via induction with 1 mM IPTG for 4 h. Cells were lysed in 50 mL of Lysis Buffer (50 mM Tris-Cl pH 8.0, 150 mM NaCl, 2 mM 2-mercaptoethanol, 10 mM imidazole, 0.1% Igepal, 2 mg/mL lysozyme, and 1 mM PMSF) for 30 min on ice. DNase I was then added to a final concentration of 1 U/mL, and cells were sonicated (60% power for 9×10 s). The DGCR8Δ protein was purified via FPLC (Akta Explore, GE Healthcare) using a HiTrap Ni-column (GE Healthcare), followed by a cation exchange column (HiTrap SP FF, GE Healthcare) and a Superdex 75 size exclusion column. The protein was concentrated and dialyzed in a Vivaspin 15 centrifugal concentrator (Sartorius Stedim Biotech) into Storage Buffer (10 mM Tris-Cl pH 7.6, 200 mM NaCl, 1 mM EDTA, and 5 mM DTI, and 30% Glycerol) and stored at −20° C.

Determination of Compound Potency via a Protein Displacement Assay.

The protein displacement assay used to identify inhibitors of the r(CGG)$_{12}$-DGCR8Δ complex is based on PubChem BioAssay AID 2675 (FIG. 3), which utilizes time resolved (TR)-FRET between antibodies that bind the RNA and the protein. The assay was conducted in IX TR-PRET Assay Buffer (20 mM HEPES pH 7.5, 110 mM KCl, 110 mM NaCl, 0.1% BSA, 2 mM MgCl$_2$, 2 mM CaCl$_2$, 0.05% Tween-20, and 5 mM DTT) with 5 μM yeast extract bulk tRNA (Roche Diagnostics), 160 nM RNA, 154.5 nM His-tagged DOCR8Δ, 40 nM Streptavidin-XL665 (HTRF, Cisbio Bioassays) and 4.4 ng/μl Anti-His$_6$-Tb (HTRF, Cisbio Bioassays).

The RNA was folded by incubation at 60° C. for 5 min in IX Folding Buffer (20 mM HEPES, pH 7.5, 110 mM KCl, and 110 mM NaCl) followed by slow cooling to room temperature. Then, DGCR8Δ and the other buffer components specified above were added to the folded RNA. After incubating for 15 min at room temperature, 9 μL of the mixture was transferred to a microcentrifuge tube containing 1 μL ligand at varying concentrations. A 9 μL aliquot of this final mixture was transferred to a well of a 384-well white plate (Greiner) and incubated for 1 h at room temperature. To exclude ligands that perturb F545/F665, a 9 μL control solution containing antibodies and different ligand concentrations in 1×TR-FRET Assay Buffer but no RNA or protein was also transferred to the plate.

Figure 8A:
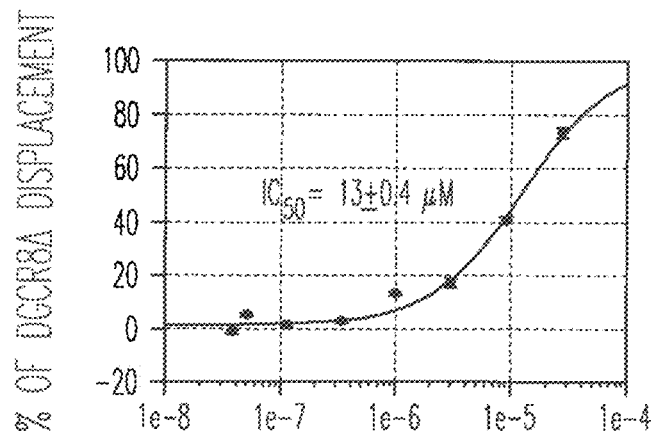
Figure 8B:
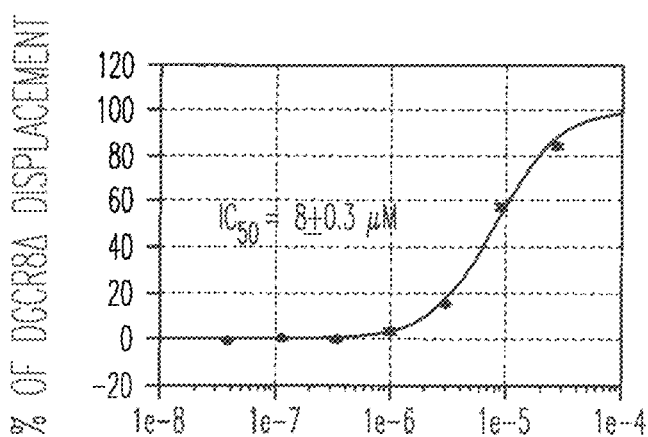

The time resolved fluorescence at 545 nm and 665 nm was measured using a SpectraMax MS plate reader (Molecular Devices, Inc.) with excitation wavelength of 345 nm, cut-off at 420 ran, 200 μs delay, and 1500 μs integration time. The ratio of fluorescence intensities at 545 nm and 665 nm (F545/F665) for a series of ligand dilutions were fit to equation 1:

$$y = B + \frac{A - B}{1 + \left(\frac{IC_{50}}{x}\right)^{hillslope}} \quad \text{(eq. 1)}$$

where y is the percentage of DGCR8Δ displacement, B is the percentage of DOCR8Δ displacement in the absence of ligand (0%), A is the maximum percentage displacement of DGCR8Δ (typically 100%), and the IC$_{50}$ is the concentration of ligand where half of the protein is displaced from the RNA. For data from compounds 1a and 1b, see FIG. 8.

Competition Dialysis.

Competition dialysis was completed as previously described (31). Briefly, 2 μM RNA or protein was transferred into Slide-a-Lyzer MINI dialysis units with a molecular weight cut-off of 2,000 (Thermo Scientific), and the units were placed into a solution of 0.7 μM ligand. Two blank units containing only buffer were used to monitor equilibration by checking the absorbance at the peak wavelength. After the blank units reached equilibrium, sodium dodecyl sulfate (SDS) was added to a final concentration of 1%, and the absorbance was measured. This absorbance was used to determine total ligand concentration ($C_t$). The concentration of the dialysate (free ligand concentration. $C_f$) was determined analogously. The bound ligand concentration ($C_b$) was then determined using equation 2:

$$C_b = C_t - C_f \quad \text{(eq. 2)}$$

where $C_b$, $C_t$, and $C_f$ are concentrations of bound, total, and free ligand, respectively.

RNA-Binding Assays Via Dye Displacement.

Dissociation constants were determined using an in-solution, fluorescence-based assay (37-45). RNA was annealed in DNA buffer (8 mM Na$_2$HPO$_4$, pH7.0, 185 mM NaCl, 0.1 mM EDTA, 40 μg/mL BSA) at 60° C. for 5 min and allowed to slowly cool to room temperature. The annealed RNA was then titrated into DNA buffer containing 1000 nM Hoechst 33258. Fluorescence signal was recorded using a Bio-Tek FLX-800 plate reader, which was equipped with excitation filter at 360/40 nm and emission filter at 460/40 nm. The change in fluorescence intensity as a function of RNA concentration was fit to the following equation (eq. 3): (37, 46)

$$I = I_0 + 0.5\Delta\epsilon\{([Ht_0]+[RNA]_0+K_t)-(([Ht]_0+[RNA]_0+K_t)^2-4[Ht]_0[RNA]_0)^{0.5}\} \quad \text{(eq. 3)}$$

where I is the observed fluorescence intensity, $I_0$ is the fluorescence intensity in the absence of RNA, $\Delta\epsilon$ is the difference between the fluorescence intensity in the absence of RNA and in the presence of infinite RNA concentration and is in units of M$^{-1}$. $[Ht]_0$ is the concentration of Hoechst 33258, $[RNA]_0$ is the concentration of the selected internal loop or control RNA, and $K_t$ is the dissociation constant.

Figure 10A:
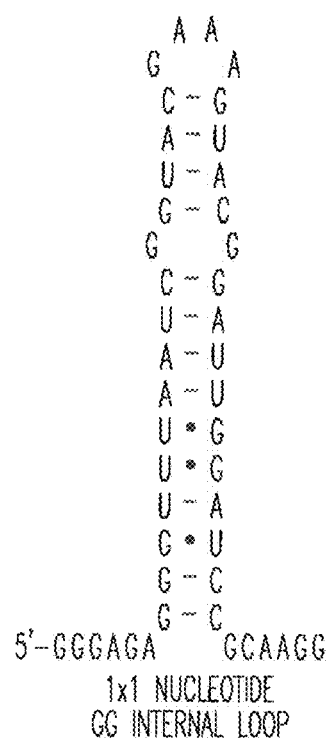
FIGS. 10A, 10B, and 10C show affinities of compounds 1a and 1b for an RNA containing one 5'CGG/3'GGC motif (SEQ ID NO:3).
Figure 10B:
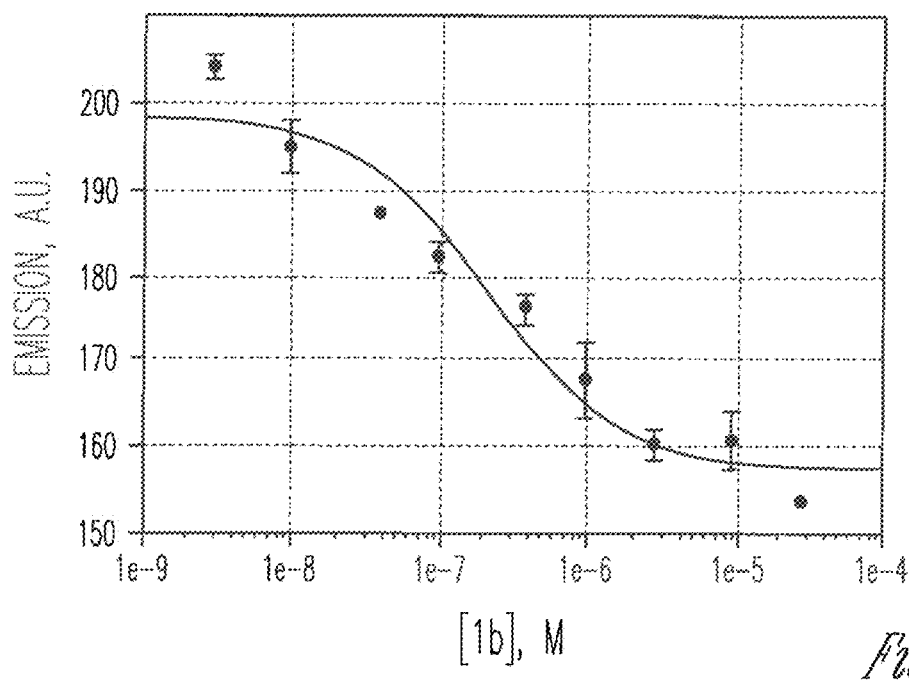
Figure 10C:
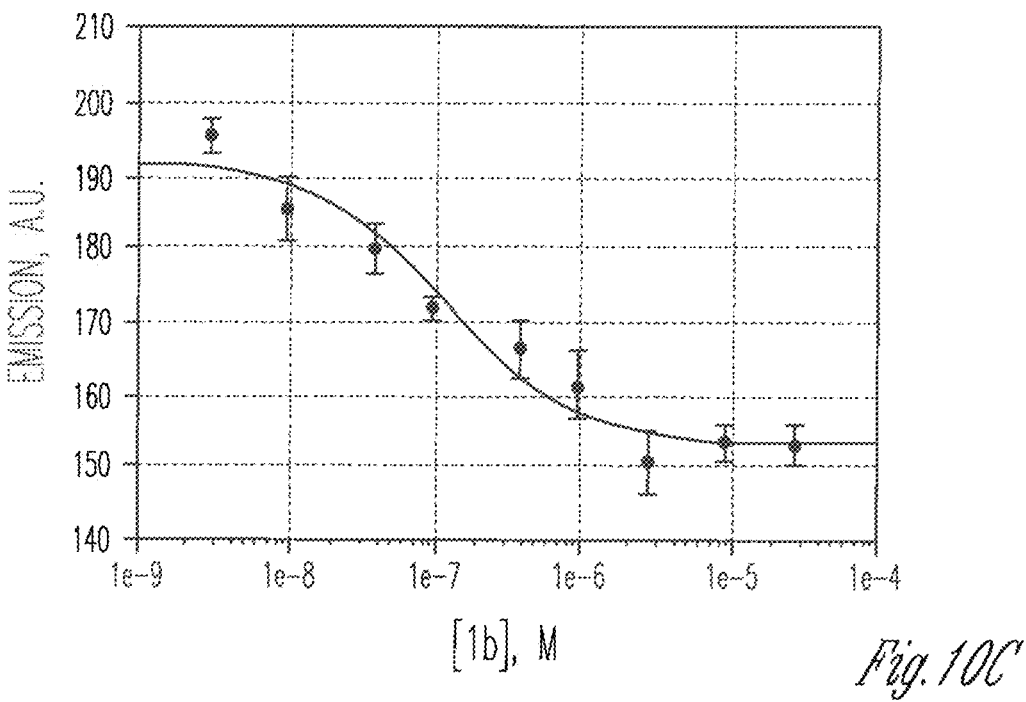

Ligands 1a-1d were then added to compete for binding to the RNA (1 μM) in presence of Hoechst 33258 (1 μM). Reduction in fluorescence of Hoechst 33258 was measured using a Bio-Tek FLX-800 plate reader as a function of ligand concentration (1a-1d) and was fit to the following equation (eq. 4): (41)

$$\theta = \frac{1}{2[Ht]_0}\left[\frac{K_t + \frac{K_t}{K_d}[C_t]_0 + [RNA]_0 + [Ht]_0 - }{\sqrt{\left(K_t + \frac{K_t}{K_d}[C_t]_0 + [RNA]_0 + [Ht]_0\right)^2 - 4[Ht]_0[RNA]_0}}\right] + A \quad \text{(eq. 4)}$$

where θ is the fraction bound of Hoechst 33258, $K_t$ is the dissociation constant for Hoechst 33258, $K_d$ is the dissociation constant of the competing ligand, $[Ht]_0$ is the total concentration of the Hoechst 33258, $[C_t]_0$ is the total concentration of the competing ligand, A is the fraction bound of Hoechst 33258 at infinite concentration of the competing ligand, and $[RNA]_0$ is the total concentration of RNA. See FIG. 10.

Improvement of Splicing Defects in a Cell Culture Model Using RT-PCR.

In order to determine if a improves FXTAS-associated splicing defects in vivo, a cell culture model system was used. Briefly. COS7 cells were grown as monolayers in 24- or 96-well plates in growth medium (1×DMEM, 10% FBS, and 1× GlutaMax (Invitrogen)). After the cells reached 90-95% confluency, they were transfected using Lipofectamine 2000 reagent (Invitrogen) or PugenHD (Roche) per the manufacturer's standard protocol. Equal amounts of a plasmid expressing a 60 CGG repeats and a mini-gene of interest (SMN2 or Bcl-x) were used. Approximately 5 h post-transfection, the transfection cocktail was removed and replaced with growth medium containing 1a. After 16-24 h, the cells were lysed in the plate, and total RNA was harvested with a Qiagen RNAEasy kit or a GenElute kit (Sigma). An on-column DNA digestion was completed per the manufacturer's recommended protocol.

A sample of RNA was subjected to reverse transcription-polymerase chain reaction (RT-PCR) using 5 units of AMV Reverse Transcriptase from Life Sciences or Superscript II (Invitrogen). Approximately 300 ng were reverse transcribed, and 150 ng were subjected to PCR. RT-PCR products were observed after 25-30 cycles of: 95° C. for 1 min: 55° C. for 1 min; 72° C. for 2 min and a final extension at 72° C. for 10 min. The products were separated by polyacrylamide or agarose gel electrophoresis, stained, and imaged using a Typhoon phosphorimager. The splicing isoforms were quantified using QuantityOne software (Bio-Rad). Table S-2 lists the RT-PCR primers used for each mini-gene construct.

Figure 11A:
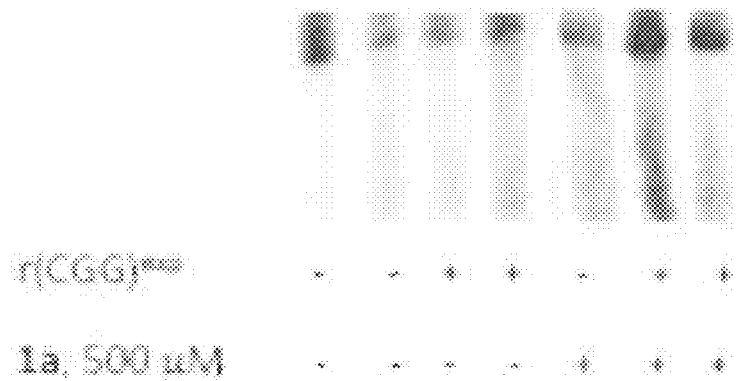
FIG. 11A: a gel electrophoresis autoradiogram.
Figure 11B:
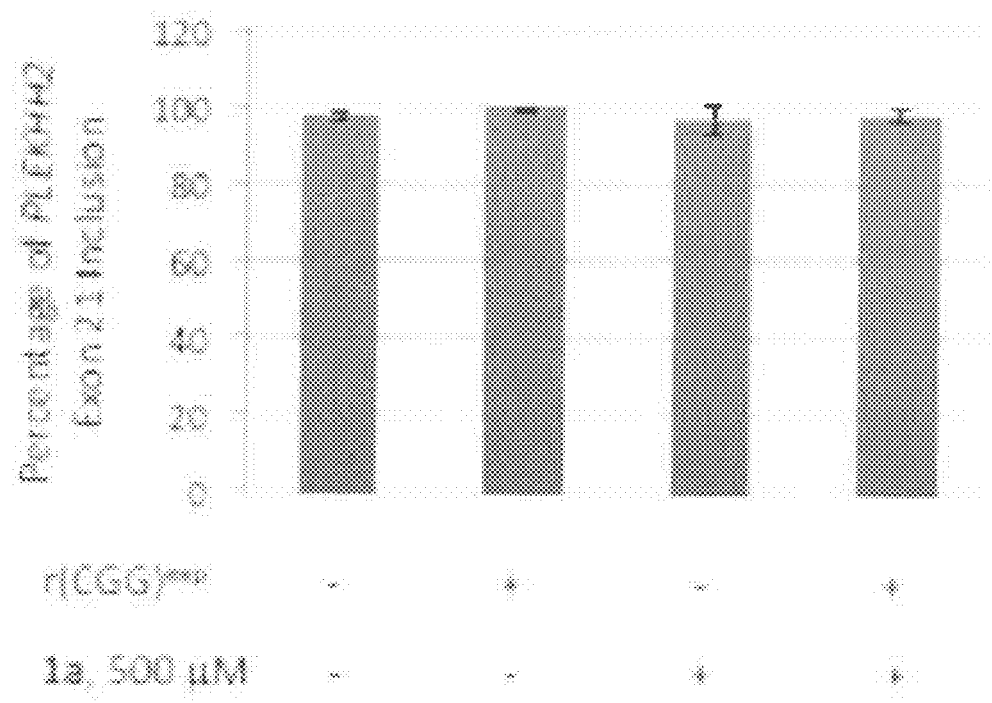
Figure 12A:
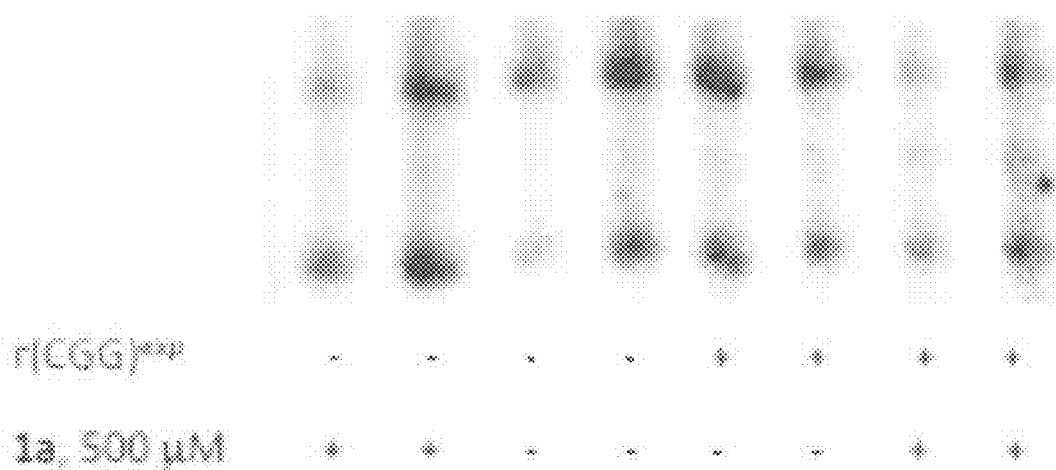
FIGS. 12A and 12B show.
Figure 12B:
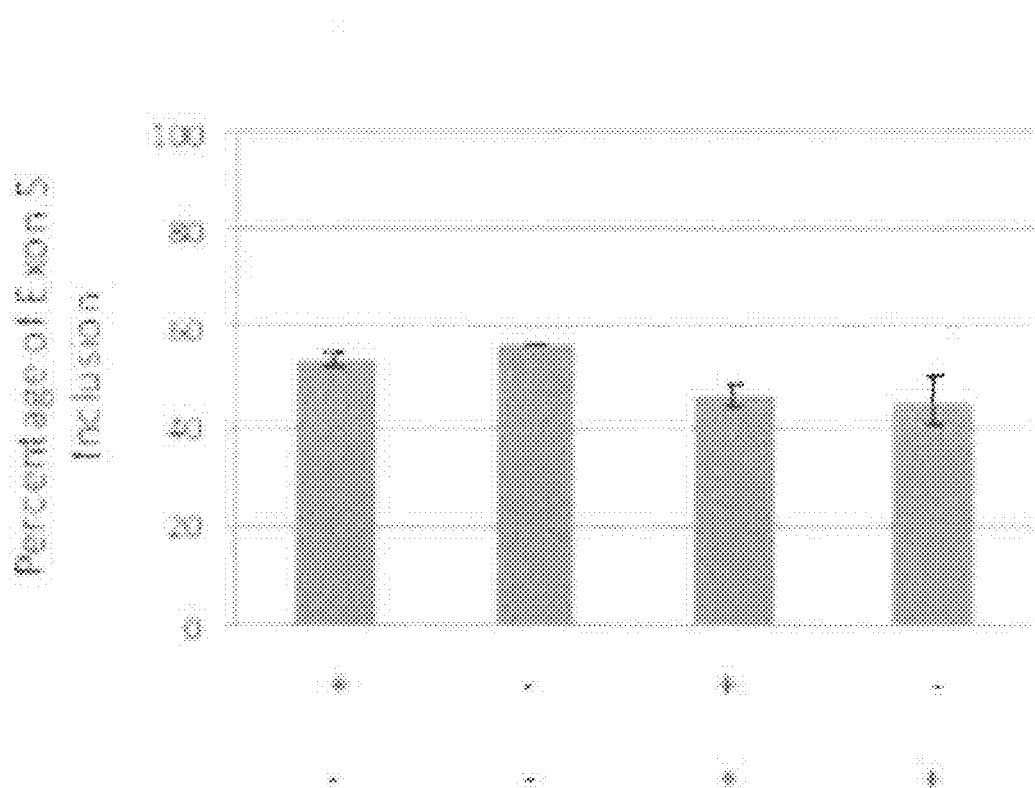

Two sets of control experiments were completed: (i) COS7 cells were co-transfected with a control plasmid that does not contain CGG repeats and the SMN2 or Bcl-x mini-gene as described above; and, (ii) COS7 cells were co-transfected with the mini-gene that expresses 60 r(CGG) repeats and a mini-gene that encodes a pre-mRNA whose splicing is not controlled by Sam68 (PLEKHH2 or cTNT) (40. Compound 1a was shown not to effect splicing of either PLEKHH2 or cTNT. See FIGS. 11 and 12.

SEQ ID NOs: 5-14 are present in the Table below.

Disruption of Nuclear Foci Using Fluorescence In Situ Hybridization (FISH).

FISH experiments were completed as previously described. (8) Briefly, COS7 cells were plated onto glass coverslips and co-transfected with plasmids encoding for $r(CGG)_{60}$ and GFP. The cells were fixed in 4% paraformaldehyde in PBS (pH 7.4) for 15 min and washed three times with PBS. Then, they were permeabilized with 0.5% Triton X-100 in PBS. Prior to addition of the FISH probe, the cells were pre-hybridized in a 2×SSC buffer containing 40% formamide and 10 mg/mL BSA for 30 min. The coverslips were hybridized for 2 h in 2×SSC buffer supplemented with 40% formamide, 2 mM vanadyl ribonucleoside, 60 µg/mL tRNA, 30 µg/mL BSA, and 0.75 µg $(CCG)_8$-Cy3 DNA oligonucleotide probe. The cells were washed twice in 2×SSC containing 50% formamide and then twice in 2×SSC. Following FISH the coverslips were incubated for 10 min in 2×SSC containing 1 µg/mL DAPI and rinsed twice in 2×SSC. The coverslips were then mounted in Pro-Long media and examined using either a simple fluorescence microscope (Leica) or a Leica DM4000 B confocal microscope.

Affinity of DGCR8Δ for Various RNAs Via Gel Mobility Shift Assays

Prior to screening the RNA-focused library for inhibition of the $r(CGG)_{12}$-DGCR8Δ complex, a gel mobility shift assay was used to determine the affinity of the protein for various RNAs. Briefly, the RNAs were radioactively labeled by in vitro transcription and [α-32P]-ATP as previously described. (48) The RNAs were folded by incubating the samples at 60° C. in 1× Gel Mobility Shift Buffer (50 mM Tris-HCl, pH 8.0, 75 mM NaCl, 37.5 mM KCl, 1 mM $MgCl_2$, 5.25 mM DTT, and 0.1 mg/mL yeast tRNA) excluding the 1 mM $MgCl_2$ followed by slow cooling on the bench top. Then, $MgCl_2$ was added to a final concentration of 1 mM and increasing amounts of DGCR8Δ were added to a total volume of 10 ILL. The samples were incubated at mom temperature for 30 min, and then 2 µL of 6× Loading Buffer (40% glycerol, 0.125% Bromophenol Blue, and 0.125% Xylene Cyanol) was added. A 10 µL aliquot of the solution was loaded on a 8% polyacrylamide (80:1 mono/bis) gel pr-chilled in ice water. The gel was run in 1×TBE for 30 min at 10 V/cm at 0° C., and subsequently dried and exposed to a phosphorimager screen. The gel was imaged using a Typhoon phosphorimager. Protein-RNA binding curves were fit to the following equation:

$$y = \frac{xB_{max}}{k_d - x}$$

TABLE 1

Primer sets used for RT-PCR analysis of alternative splicing.

Figure 9B:
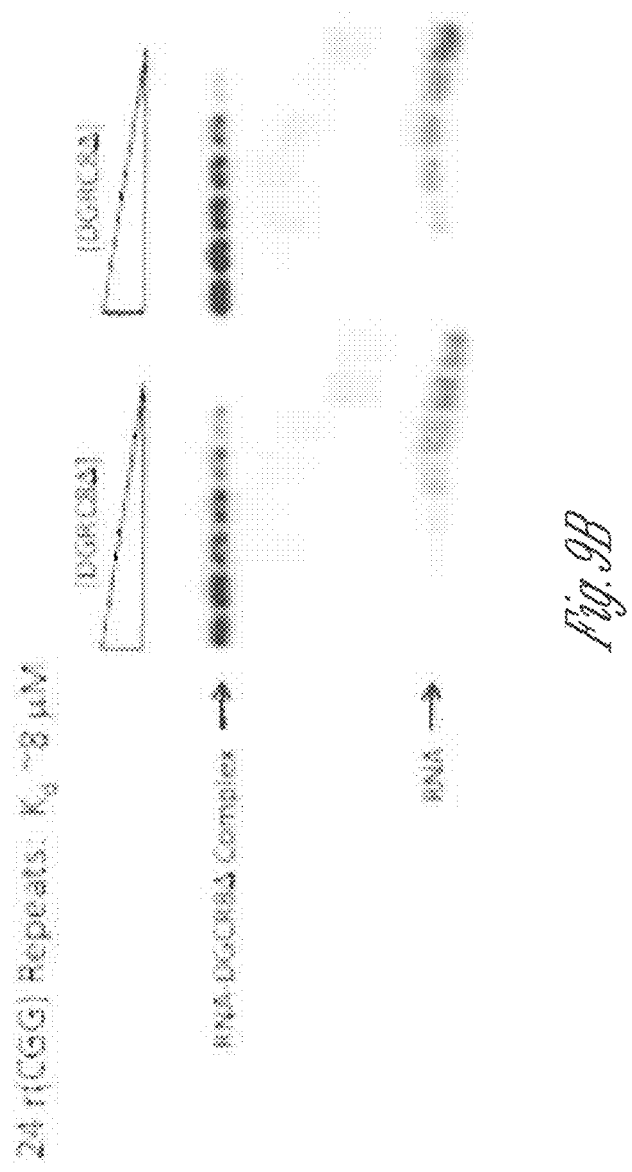
Figure 9C:
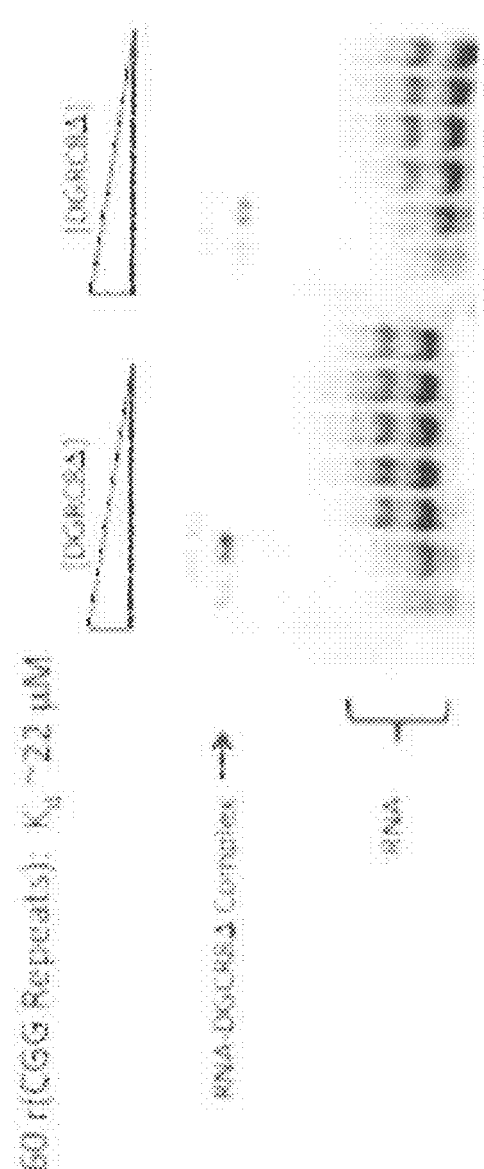

| Gene | Forward Primer | Reverse Primer |
|---|---|---|
| SMN2 mini-gene | 5' GGT GTC CAC TCC CAG TTC AA | 5' GCC TCA CCA CCG TGC TGG |
| Bcl-x mini-gene | 5' GGA GCT GGT GGT TGA CTT TCT | 5' TAG AAG GCA CAG TCG AGG |
| cTNT mini-gene | 5' GTT CAC AAC CAT CTA AAG CAA GAT G | 5' GTT GCA TGG CTG GTG CAG G |
| PLEKHH2 mini-gene | 5' CGG GGT ACC AAA TGC TGC AGT TGA CTC TCC | 5' CCG CTC GAG CCA TTC ATG AAG TGC ACA GG |
| INSR mini-gene | 5' GTA CAA GCT TGA ATG CTG CTC CTG TCC AAG ACA G | 5' GCC CTC GAG CGT GGG CAC GCT GGT C | where y is a percentage of bounded DGCR8Δ, x is the concentration of protein. Bmax is maximum percentage of protein bound (restrained to equal 100%), and Kd is disassociation constant, which is approximately equal to protein concentration where 50% of maximum binding is achieved. FIG. 9 shows results of the Gel Mobility Shift Assays, showing that DGCR8Δ binds to RNAs with different numbers of r(CGG) repeats similarly.

Kinetic Studies Using Surface Plasmon Resonance.

On rates, off rates and $K_{obs}$ values were measured using a ForteBio OctetRed spectrophotometer and Streptavidin SA dip-and-read biosensors (ForteBio). Sensors were pre-equilibrated in 1× Kinetics Buffer (ForteBio) prior to beginning measurements, 5'-Biotinylated r(CGG)$_{12}$ was folded by heating in IX Kinetics Buffer at 65° C. for 5 min followed by slow cooling to room temperature on the bench top. Measurements were completed by incubating sensors sequentially in 200 μL of: 1× Kinetics Buffer, 540 nM 5'-biotinylated r(CGG)$_{12}$, 1× Kinetics Buffer, compound of interest (varying concentrations; 1:2 dilutions in 1× Kinetics Buffer), and finally IX Kinetics Buffers. Data were fit using ForteBio's Data Analysis 7.0 software. Data were fit using a 2:1 heterogeneous ligand model. This model fits the binding of one analyte in solution to two different binding sites on the surface. Kinetic parameters are calculated for both of the interactions.

Small Molecules.

All small molecules 1a-1e were procured from the National Cancer Institute (NCI), Compound 1f, 9-hydroxyellipticine, was obtained from The Scripps Research Institute and from VWR, Inc.

Compounds of the invention of formula (I), of compounds that are analogs or derivatives of 9-hydroxyellipticine bearing an N-substituted pyridinium moiety, can be prepared according to ordinary knowledge in conjunction with the disclosures herein, by a person of ordinary skill in the art of organic synthesis.

The compound 9-hydroxyellipticine is a known compound of formula (A1):

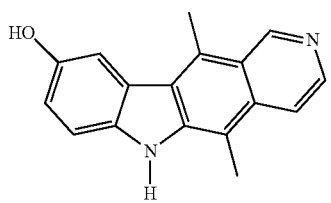

(A1)

having PubChem Compound ID: 91643; CAS Registry Number 52238-35-4. It is commercially available, e.g., from Santa Cruz Biotechnology, Inc., catalog number sc-203940, 2145 Delaware Avenue, Santa Cruz, Calif. 95060. U.S.A.

The N-methyl pyridinium analog of ellipticine, also known as elliptinium, as its acetate salt, of formula (A2):

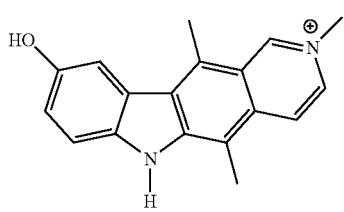

(A2)

is also a known compound, having Pubchem Compound ID: 42722; CAS Registry Number 58337-35-2.

Synthesis of Compounds for Practice of Methods of the Invention

Compounds for practicing methods of the invention include analogs or derivatives of 9-hydroxyelliptcine bearing an N-substituted pyridinium moiety.

It is within ordinary skill to prepare compounds of this structural class or motif from ellipticine, via (1) protection of the phenolic hydroxyl group with an O-protecting group, such as are well known in the art; (2) alkylation of the pyridine nitrogen atom with a suitable alkylating agent; then (3) deprotection of the phenolic hydroxyl group. Suitable alkylating agents, such as are well known in the art, can include various organic halides, sulfonate esters, and the like. For example, reaction of an O)-protected ellipticine with benzyl bromide, followed by O-deprotection, can provide the N-benzyl pyridinium analog of ellipticine, such as can be used in practicing methods of the invention, or as is a compound of the invention. Similarly, various substituted benzyl bromides can be used to prepare substituted N-benzylpyridinium analogs of ellipticine, following O-deprotection, as shown in Synthetic Scheme 1, below.

The synthesis of compounds of the invention, or compounds suitable for practicing methods of the invention, can be prepared according to the above scheme. The starting material, 9-hydroxyellipticine, is a commercially available compound. In these structures, $R^3$ and $R^4$ of formula (I), above, are both methyl, the phenol bears hydrogen ($R^1$), and the indole nitrogen bears a hydrogen ($R^2$). First, the phenolic hydroxyl group of 9-hydroxyellipticine is protected with O-protecting group G, options for which are described in greater detail above, such as are well-known in the art, to provide the O-protected compound A. This intermediate can then be N-alkylated, selectively on the pyridine nitrogen atom, to provide the quaternized pyridinium species B.

As is well-known in the art, the electron-rich pyridine moiety is more readily alkylated than is the electron-deficient indole moiety. O-deprotection yields the parent compound C, wherein $R^1$, $R^2$ and hydrogen and $R^3$, $R^4$ are methyl. $R^5$ can be any suitable group, wherein X is a leaving group such as halo, sulfonate ester, and the like; providing a reagent useful to alkylate the pyridine nitrogen atom.

For example, $R^5$ can be alkyl, or aminoalkyl, or heteroarylalkyl, or the like. It is within ordinary skill to prepare and use a wide range of $R^5$—X reagents for alkylation of the pyridine nitrogen atom of 9-hydroxyellipticine. O-deprotection provides the compound C, which includes 9-hydroxyellipticinium compounds of the invention. Further reaction of compound C can provide the 9-hydroxyellipticinium compounds bearing a phenolic ether or ester (i.e., $R^1$ is alkyl or alkanoyl), compound D, which can be further elaborated under more stringent reaction conditions to provide compounds of the invention in which the indole nitrogen atom bears an alkyl or acyl group (i.e., $R^2$ is alkyl or alkanoyl).

Synthetic Scheme I: Synthesis of ellipticine derivatives from 9-hydroxyellipticine

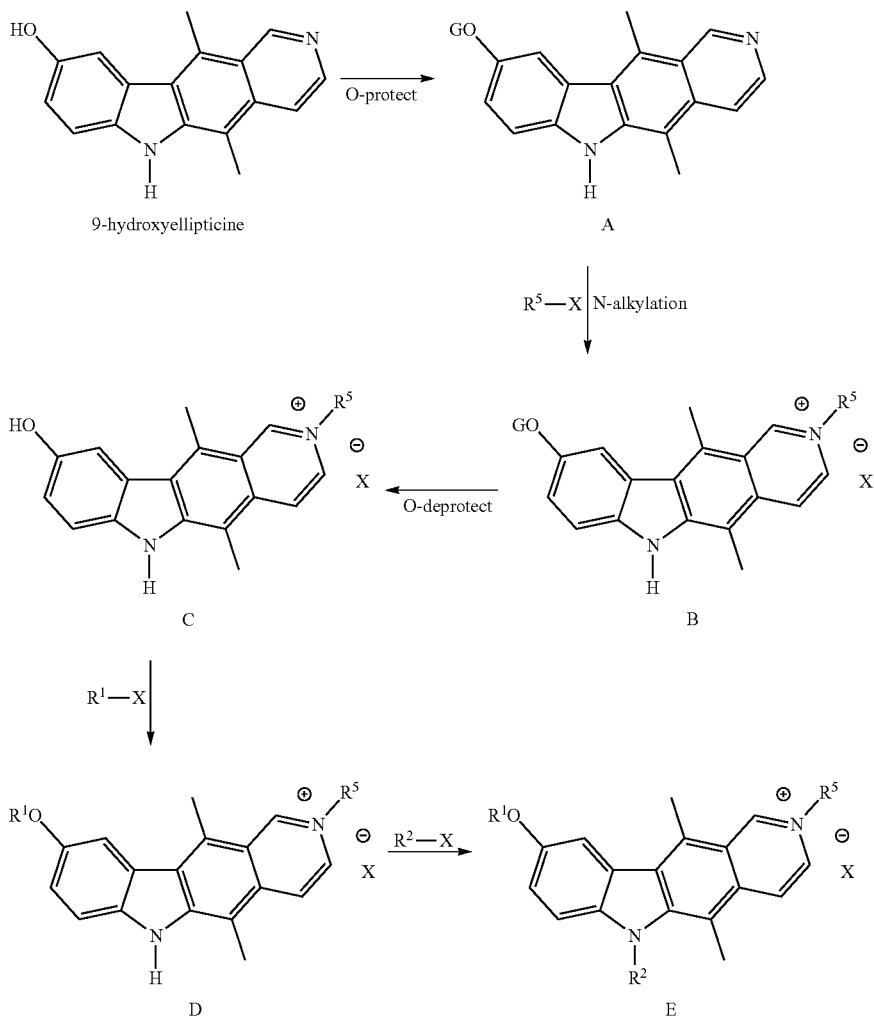

For preparation of compounds of the invention wherein $R^3$ and $R^4$ are other than the methyl groups found in the ellipticine alkaloids, the person of ordinary skill can use total synthesis, as shown in Synthetic Scheme II, below.

For further details, see: *Heterocylic chemistry*, 48, 814, (2011); the route from that product to the product of reaction "h" is described in *Synthesis*, page 1221 (1992). By use of reagents other than hexane-2,5-dione in step a, final products with $R^3$ and $R^4$ groups other than methyl can readily be obtained by the person of ordinary skill; e.g. compounds with hydrogen or with various alkyl, haloalkyl, alkoxyalkyl, haloalkoxyalkyl, and/or aryl groups as groups $R^3$ and $R^4$. When a dione other than hexane-2,5-dione is used in Step a of Synthetic Scheme II, the indole product of that reaction will comprise analogs of the reaction product shown wherein $R^3$ and $R^4$ are other than methyl. Carrying this intermediate through to the product of Step h yield an analog of 9-hydroxyellipticine, wherein $R^3$ and $R^4$ are the groups incorporated in Step a, e.g., other alkyl groups, aryl groups, heteroaryl groups, and the like. This intermediate can be converted into the N-alkylpyridinium species as indicated in Synthetic Scheme I.

Synthetic Scheme II: Total Synthesis of Ellipticine Derivatives

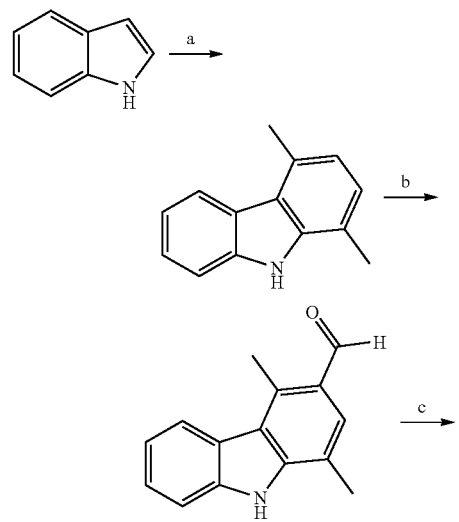

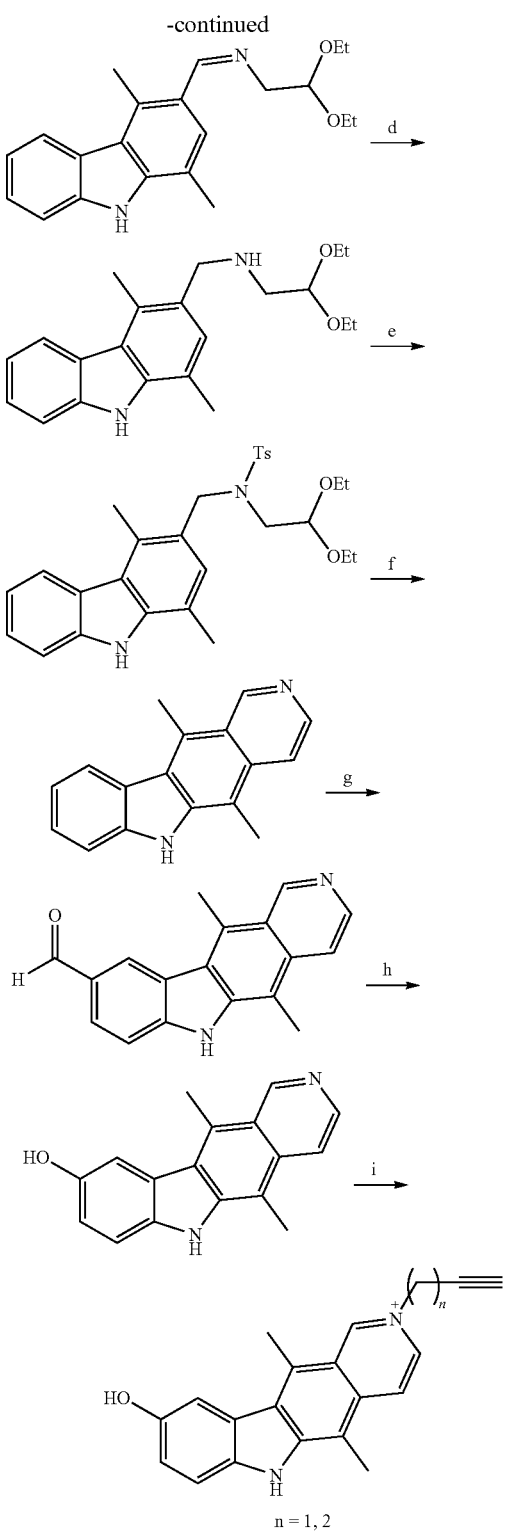

Reagents and conditions: (a) hexane-2,5-dione, p-TsOH, EtOH, reflux; (b) POCl₃, DMF, chlorobenzene, reflux; (c) aminoacetaldehyde diethylacetal, 110° C.; (d) PtO₂, H₂, EtOH, r.t. at 20 psi; (e) p-TsCl, pyridine, rt.; (f) HCl, dioxane, reflux; (g) HMTA/TFA, reflux, (h) H₂SO₄/H₂O₂, MeOH, reflux, (i) 3-iodoprop-1yne (or 4-iodobut-1-yne), DMF In some instances, using highly reactive alkylating agent such as the propargyl halide shown in Step i of Synthetic Scheme II, O-protection is not necessary, as selective N-alkylation can be achieved, for example, to yield the N-propargyl pyridinium product of Step i of Synthetic Scheme II.

The reactive triple bond of this propargyl species can be used as a precursor for further elaboration of heteroaryl-comprising $R^5$ groups, such as by the use of click chemistry and the acetylene-azide click reaction, to yield triazole-alkyl groups at position $R^5$. The triazole itself can bear additional groups, e.g., additional amino groups and the like, through use of the appropriate azido precursor, as is apparent to a person of skill in the art of organic synthesis.

For synthesis of the dimeric compounds of formula (II), FIG. 13 shows a synthetic scheme that in conjunction with ordinary knowledge of the person having skill in the art serves to teach how to prepare compounds of formula (II) of the invention. In FIG. 13, the steps are as follows: Synthetic scheme of E-alkyne: (a) hexane-2,5-dione, p-TsOH, EtOH, reflux; (b) POCl₃, DMF, chlorobenzene, reflux; (c) aminoacetaldehyde diethylacetal, 110° C.; (d) NaBH4; (e) p-TsCl, pyridine, rt.; (f) HCl, dioxane, reflux; (g) HMTA/TFA, reflux; (h) H₂SO₄/H₂O₂, MeOH, reflux, 52%; (i) 3-byromoprop-1-yne, DMF, 62%. B. synthetic scheme of 2E-nNMe: (j) 20% piperizine/DMF: 2-bromoacetic acid, DIC, DIPEA/DMF, microwave: (k) 3-azidopropylamine/DMF, microwave; (l) Fmoc-N-methyl-L-alanine. DIC, HOAt, DIEA/DMF, microwave at 75° C.; 20% piperizine/DMF; (m) 2-bromoacetic acid, DIC, DIPEA/DMF, microwave; 3-azidopropylamine/DMF, microwave; (n) 30% TFA/CH₂Cl₂; HPLC purification; (o) CuSO₄, Na ascorbate, TBTA/H₂O:tBuOH=1:1, sonication.

The reactive triple bond of the propargyl species, termed the E-alkyne herein, can undergo the acetylene-azide click reaction, e.g., copper-catalyzed click reaction, to form the triazole rings of the linker L of formula LI as described above.

Synthesis.

Fmoc-Rink amide resin (059 mmol/g) was purchased from Advanced ChemTech. N,N-dimethylformamide (DMF, anhydrous) was purchased from EMD and used without further purification. Piperidine, trifluoroacetic acid (TFA), N,N-diisopropylethyl amine (DIEA), and 2-bromoacetic acid were purchased from Sigma Aldrich. N,N'-diisopmpylcarbodiimide (DIC) and 1-hydroxy-7-azabenzotriazole (HOAt) were purchased from Advanced ChemTech. Fmoc-N-methyl-L-alanine was purchased from Combi-Blocks, 9-Hydroxyellipticine was synthesized as reported previously, (22, 23)N-methyl alanine peptides were synthesized using a Biotage Initiator+ SP Wave microwave.

Compound Purification and Analysis.

Preparative HPLC was performed using a Waters 1525 Binary HPLC pump equipped with a Waters 2487 dual absorbance detector system and a Waters Sunfire C18 OBD 5 μm 19×150 mm column. Absorbance was monitored at 315 and 220 nm. A gradient of 20-100% MeOH in H₂O with 0.1% TFA over 60 min was used for compound purification. Analytical HPLC was performed using a Waters Symmetry C18 5 μm 4.6×150 mm column. Compounds were analyzed using a gradient of 20-100% MeOH in H₂O with 0.1% TFA over 60 min. All compounds evaluated had ≥95% purity by analytical HPLC. Mass spectrometry was performed with an Applied Biosystems MALDI ToF/ToF Analyzer 4800 Plus using an α-hydroxycinnamic acid matrix.

Synthesis of N-Methyl-L-Alanine Peptide Backbone.

Deprotected Rink amide resin (200 mg, 0.12 mmol) was shaken with a solution of 1 M bromoacetic acid (2 mL) and DIC (250 μL, 1.5 mmol) in DMF (2 mL) via microwave irradiation (3×15 s) using a 700 W microwave set to 10% power. The resin was washed with DMF (3×5 mL) and reacted twice with a solution of 3-azidopropylamine (250 µL, 0.6 mmol) in DMF (2 mL) via microwave irradiation (3×15 s) using a 700 W microwave set to 10% power. The resin was washed with DMF (3×5 mL). Then a solution of Fmoc-N-methyl-L-alanine (100 mg, 03 mmol), DIC (48 µL, 0.9 mmol), HOAt (41 mg, 0.9 mmoL), and DIEA (104 µL, 0.9 mmol) in DMF (2 mL) was added and the reaction heated via microwave to 75° C. for 10 min. The resin was washed with DMF and the FMOC was removed with 20% piperidine/DMF (2×10 min). This cycle was repeated until a desired number of N-methyl-L-alanine was added. The resin was shaken with a solution of 1 M bromoacetic acid (2 mL) and DIC (250 µL, 1.5 mmol) in DMF (2 mL) via microwave irradiation (3×15 s) using a 700 W microwave set to 10% power. The resin was washed with DMF (3×5 mL) and reacted twice with a solution of 3-azidopropylamine (250 µL, 0.6 mmol) in DMF (2 mL) via microwave irradiation (3×15 s) using a 700 W microwave set to 10% power. The peptides were cleaved from the resin by 30% TFA/CH$_3$Cl$_2$ and purified by HPLC.

Synthesis of 9-hydroxy-N-propargylellipticine

Into the solution of 9-hydroxyellipticine (100 mg, 038 mmol) in DMF, was added propargyl bromide (023 mL, 2.1 mmol) and the solution stirred overnight at room temperature. After diethyl ether was added, the product (62%) was obtained by filtration. $^1$H-NMR (400 MHz, DMSO-d6) δ 2.82 (s, 3Hs), 3.26 (s, 3Hs), 3.98 (s, 1H), 5.69 (s, 2Hs), 7.17 (dd, 1H, 1=8 Hz, J=4 Hz), 7.51 (d, 1H, J=8 Hz), 7.81 (d, 1H, J=4 Hz), 8.49 (d, 2H, J=4 Hz), 9.43 (s, 1H), 10.12 (s, 1H), 12.03 (a, 1H). $^{13}$C-NMR (400 MHz, DMSO-d6) δ 11.95, 14.84, 48.35, 76.95, 80.12, 109.77, 110, 32, 112.22, 117.57, 119.49, 120.55, 122.93, 126.21, 129.88, 132.16, 134.05, 136.04, 145.19, 146.50, 152.19.

General procedure for 9-hydroxy-N-propargylellipticine conjugation to peptide tertiary amides Peptide backbone was dissolved in a 1:1 mixture of tBuOH and H$_2$O and CuSO$_4$, sodium ascorbate, TBTA and 9-hydroxy-N-propargylellipticine were added in the solution. The mixture was sonicated for 3 hours and the conjugate was purified by using reverse phase HPLC with 20-75% MeOH/H$_2$O+0.1% (v/v) TFA over 40 min.

Characterization of Compounds for Practice of Methods of the Invention

The purities of the compounds used in additional studies (IC$_{50}$'s, affinities, etc.) were determined by HPLC, and their masses were confirmed by ESI mass spectrometry. All compounds were ≥95% pure. Mass spectra were collected on a Varian 500 MS spectrometer equipped with Varian Prostar Autosampler 410. The purities of compounds were determined by analytical HPLC using a Waters 1525 Binary HPLC Pump equipped with Waters 2487 Dual λ Absorbance Detector system and the following conditions: a Waters Symmetry C8 5 µm 4.6×150 mm column, room temperature, flow rate 2.4 ml/min, and a linear gradient of 0-100% B in A for 60 min. A is water, B is methanol.

These data are shown below in Table S-2.

TABLE S-2

Characterization of 1a and derivatives thereof including HPLC retention times, and calculated and observed masses.

| Compound | Molecular Formula | HPLC Retention Time (min) | MS (Calculated) | ES(+)-MS (Found) |
|---|---|---|---|---|
| 1a | C$_{24}$H$_{28}$N$_3$O$^+$ | 21 | 374.2 (M) | |
| 1b | C$_{23}$H$_{28}$N$_3$O$^+$ | 14 | 362.2 (M) | 362.3 (M) |
| 1c | C$_{19}$H$_{19}$N$_2$O$^+$ | 18 | 291.2 (M) | 291.2 (M) |
| 1d | C$_{18}$H$_{17}$N$_2$O$^+$ | 17 | 277.1 (M) | 277.1 (M) |
| 1e | C$_{17}$H$_{14}$N$_2$O | 29 | 263.1 (M + H)$^+$ | 263.1 (M + H)$^+$ |
| 1f | C$_{17}$H$_{14}$N$_2$ | 32 | 247.1 (M + H)$^+$ | 247.1 (M + H)$^+$ |

Evaluations

It is within ordinary skill using the procedures provided herein and in references cited herein, which are incorporated by reference in their entireties, to evaluate any compound disclosed and claimed herein for effectiveness for in vivo evaluation of bioactivity of r(CGG)$^{exp}$-binding small molecules, as well as in the various cellular assays found in the scientific literature. Accordingly, the person of ordinary skill, using the disclosure of the present application in conjunction with the disclosures of documents cited herein, and the knowledge of the person of ordinary skill, can prepare and evaluate any of the claimed compounds for effectiveness as a potential human therapeutic agent, without undue experimentation.

Any r(CGG)$^{exp}$-binding small molecule compound found to be effective as an bioactive agent can likewise be further tested in animal models, and in human clinical studies, using the skill and experience of the investigator to guide the selection of dosages and treatment regimens.

Pharmaceutical Compositions of the Invention and for Use in Methods of the Invention Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient that can be a carrier or a diluent. For example, the active compound will usually be mixed with a carrier, or diluted by a carrier, or enclosed within a carrier that can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents that do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that can be prepared by conventional tableting techniques can contain:

| Core: | |
| --- | --- |
| Active compound (as free compound or salt thereof) | 250 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

DOCUMENTS CITED

1. Atkins, J. F., Gesteland, R. F., and Cech, T. R., (Eds.) (2011) *RNA Worlds: From Life's Origins to Diversity in Gene Regulation,* 3rd ed., Cold Spring Harbor Laboratory Press
2. Cooper, T. A., Wan, L. L., and Dreyfuss, G. (2009) RNA and Disease, *Cell* 136, 777-793.
3. Calin, G. A., and Croce. C. M. (2006) MicroRNAs and chromosomal abnormalities in cancer cells, *Oncogene* 25, 6202-6210.
4. Wilton, S. D., and Fletcher, S. (2005) RNA splicing manipulation: strategies to modify gene expression for a variety of therapeutic outcomes, *Curr Gene Ther* 5, 467-483.
5. Orr, H. T., and Zoghbi, H. Y. (2007) Trinucleotide repeat disorders, *Annu Rev Neurosci* 30, 575-621.
6. Bates. G. (2003) Huntingtin aggregation and toxicity in Huntington's disease, *Lancet* 361, 1642-1644.
7. Jin, P., Allich, R. S, and Warren, S. T. (2004) RNA and microRNAs in fragile X mental retardation, *Nat Cell Biol* 6, 1048-1053.
8. Sellier, C., Rau, P., Liu, Y., Tassone, F., Hukema, R. K., Gattoni, R., Schneider, A., Richard. S., Willemsen. R., Elliott. D. J., Hagerman, P. J., and Charlet-Berguerand, N. (2010) Sam68 sequestration and partial loss of function are associated with splicing alterations in FXTAS patients, *EMBO J* 29, 1248-1261.
9. Mankodi, A., Logigian, E., Callahan. L., McClain, C., White, R., Henderson, D., Krym. M., and Thornton, C. A. (2000) Myotonic dystrophy in transgenic mice expressing an expanded CUG repeat, *Science* 289, 1769-1773.
10. Kumar, A., Parkesh, R., Sznajder, L J., Childs-Disney, J. L., Sobczak, K., and Disney, M. D. (2012) Chemical Correction of Pre-mRNA Splicing Defects Associated with Sequestration of Muscleblind-like 1 Protein by Expanded r(CAG)-Containing Transcripts, *ACS Chem Biol.* 2012 Mar. 16; 7(3):496-505. Epub 2012 Jan. 17.
11. Parkesh, R., Childs-Disney, J. L., Nakamori, M., Kumar, A., Wang, E., Wang. T., Hoskins, J., Housman, D. E., Thornton, C. A., Disney, M. D., and Tran, T. (2012) Design of a Bioactive Small Molecule that Targets the Myotonic Dystrophy Type 1 RNA Via an RNA Motif-Ligand Database & Chemical Similarity Searching, *J Am Chem Soc.* 2012 Mar. 14; 134(10):4731-42. Epub 2012 Mar. 5.
12. Childs-Disney, J. L., Hoskins, J., Rzuczek, S., Thornton, C., and Disney. M. D. (2012) Rationally Designed Small Molecules Targeting the RNA that Causes Myotonic Dystrophy Type 1 Are Potently Bioactive, *ACS Chem Biol.* 2012 May 18; 7(5):856-62. Epub 2012 Mar. 5.
13. Cho, J., and Rando, R. R. (2000) Specific binding of Hoechst 33258 to site 1 thymidylate synthase mRNA, *Nucleic Acids Res* 28, 2158-2163.
14. Pushechnikov, A., Lee, M. M., Childs-Disney, J. L., Sobczak, K., French, J. M., Thornton, C. A., and Disney, M. D. (2009) Rational design of ligands targeting triplet repeating transcripts that cause RNA dominant disease: application to myotonic muscular dystrophy type 1 and spinocerebellar ataxia type 3, *J Am Chem Soc* 131, 9767-9779.
15. Warf, M. B., Nakamori, M., Matthys, C. M., Thornton, C. A., and Berglund. J. A. (2009) Pentamidine reverses the splicing defects associated with myotonic dystrophy, *Proc Natl Acad Sci USA* 106, 18551-18556.
16. Bostrom, J., Greenwood, J. R., and Gottfries, J. (2003) Assessing the performance of OMEGA with respect to retrieving bioactive conformations. *J Mol Graph Model* 21, 449-462.
17. Grant, J. A., Gallardo, M. A., and Pickup, B. T. (1996) A fast method of molecular shape comparison. A simple application of a Gaussian description of molecular shape, *J Comput Chem* 17, 1653-1666.
18. Haigh, J. A., Pickup, B. T., Grant, J. A., and Nicholls, A. (2005) Small molecule shape-fingerprints *J Chem Inf Model* 45, 673-684.
19. Mills, J. B., and Dean, P. M. (1996) Three-dimensional hydrogen-bond geometry and probability information from a crystal survey, *J Comput Aided Mol Des* 10, 607-622.
20. Sellier, C., Rau, F., Liu, Y. L., Tassone, F., Hukema, R. K., Gattoni, R., Schneider. A., Richard, S., Willemsen, R., Elliott, D. J., Hagerman, P. J., and Charlet-Berguerand, N. (2010) Sam68 sequestration and partial loss of function are associated with splicing alterations in FXTAS patients, *Embo Journal* 29, 1248-1261.
21. Sobczak, K., Michlewski, G., de Mezer, M., Kierzek, E., Krol, J., Okljniczak, M., Klerzek, R., and Krzyzosiak, W. J. (2010) Structural diversity of triplet repeat RNAs, *J Biol Chem* 285, 12755-12764.
22. Tassone, F., Hagerman, R. J., Loesch, D. Z., Lachiewicz. A., Taylor, A. K., and Hagerman. P. J. (2000) Fragile X males with unmethylated, full mutation trinucleotide repeat expansions have elevated levels of FMR1 messenger RNA, *Am J Med Genet* 94, 232-236.
23. Tassone, F., Hagerman, R. J., Taylor, A. K., and Hagerman, P. J. (2001) A majority of fragile X males with methylated, full mutation alleles have significant levels of FMR1 messenger RNA. *J Med Genet* 38, 453-456.
24. Willemsen, R., Hoogeveen-Westerveld, M., Reis, S., Holstege, J., Severijnen, L A., Nieuwenhuizen, I. M., Schrier, M., van Unen, L., Tassone, F., Hoogeveen, A. T., Hagerman, P. J., Mientjes, E. J., and Oostra, B. A. (2003) The FMR1 CGG repeat mouse displays ubiquitin-positive intranuclear neuronal inclusions; implications for the cerebellar tremor/ataxia syndrome, *Hum Mol Genet* 12, 949-959.
25. Jin, P., Zarnescu, D. C., Zhang, F., Pearson. C. E., Lucchesi, J. C., Moses, K., and Warren, S. T. (2003) RNA-mediated neurodegeneration caused by the fragile X premutation rCGG repeats in *Drosophila, Neuron* 39, 739-747.
26. Jin, P., Duan, R., Qurashi, A., Qin, Y., Tian. D., Rosser, T. C., Liu, H., Peng, Y., and Warren, S. T. (2007) Pur alpha binds to rCGG repeats and modulates repeat-mediated neurodegeneration in a *Drosophila* model of fragile X tremor/ataxia syndrome, *Neuron* 55, 556-564.
27. Tassone, F., Hagerman, R. J., Garcia-Arocena, D., Khandjian, E. W., Greco, C. M., and Hagerman, P. J. (2004) Intranuclear inclusions in neural cells with premumation alleles in fragile X associated tremor/ataxia syndrome, *J Med Genet* 41, e43.
28. Greco, C. M., Berman, R. F., Martin, R. M., Tassone, F., Schwartz. P. H., Chang, A., Trapp, B. D., Iwahashi, C., Brunberg, J., Grigsby, J., Hessl, D., Becker, E. J., Papazian, J., Leebey, M. A., Hagerman, R. J., and Hagerman, P. J. (2006) Neuropathology of fragile X-associated tremor/ataxia syndrome (FXTAS), *Brain* 129, 243-255.

29. Sellier, C., Hagerman, P., Willemsen, R., and Charlet-Berguerand, N. DROSHA/DGCR8 sequestration by expanded CGG repeats leads to global micro-RNA processing alteration in FXTAS patients [abstract], *12th International Fragile X Conference*, Detroit, Mich.
30. Chawla, G., Lin, C. H., Han, A., Shiue, L., Ares, M., Jr., and Black, D. L. (2009) Sam68 regulates a set of alternatively spliced exons during neurogenesis, *Mol Cell Biol* 29, 201-213.
31. Chaires. J. B., Ragazzon, P. A., and Garbett, N. C. (2003) A competition dialysis assay for the study of structure-selective ligand binding to nucleic acids, *Curr Protoc Nucleic Acid Chem Chapter* 8, Unit 8 3.
32. Philips, A. V., Timchenko, L. T., and Cooper, T. A. (1998) Disruption of splicing regulated by a CUG-binding protein in myotonic dystrophy, *Science* 280, 737-741.
33. McLennan, Y., Polussa, J., Tassone, F., and Hagerman, R. (2011) Fragile x syndrome, *Curr Genomics* 12, 216-224.
34. Peyret. N., Seneviratne, P. A., Allawi, H. T., and Santa-Lucia, J., Jr. (1999) Nearest-neighbor thermodynamics and NMR of DNA sequences with internal A.A. C.C, G.G, and T.T mismatches, *Biochemistry* 38, 3468-3477.
35. SantaLucia, J., Jr. (1998) A unified view of polymer, dumbbell, and oligonucleotide DNA nearest-neighbor thermodynamics, *Proc Natl Acad Sci USA* 95, 1460-1465.
36. Puglisi, J. D., and Tinoco, L, Jr. (1989) Absorbance melting curves of RNA, *Methods Enzymol* 180, 304-325.
37. Disney, M. D., Labuda, L. P., Paul, D. J., Poplawski, S. G., Pushechnikov, A., Tran, T., Velagapudi, S. P., Wu, M., and Childs-Disney. J. L. (2008) Two-dimensional combinatorial screening identifies specific aminoglycoside-RNA internal loop partners, *J Am Chem Soc* 130, 11185-11194.
38. Tran, T., and Disney, M. D. (2011) Two-dimensional combinatorial screening of a bacterial rRNA A-site-like motif library: defining privileged asymmetric internal loops that bind aminoglycosides, *Biochemistry* 49, 1833-1842.
39. Aminova, O., Paul, D. J., Childs-Disney, J. L., and Disney, M. D. (2008) Two-dimensional combinatorial screening identifies specific 6'-acylated kanamycin A- and 6'-acylated neamine-RNA hairpin interactions, *Biochemistry* 47, 12670-12679.
40. Tran, T., and Disney, M. D. (2011) Molecular recognition of 6'-N-5-hexynoate kanamycin A and RNA 1×1 internal loops containing CA mismatches, *Biochemistry* 50, 962-969.
41. Childs-Disney, J. L, Wu, M., Pushechnikov, A., Aminova, O., and Disney, M. D. (2007) A small molecule microarray platform to select RNA internal loop-ligand interactions, *ACS Chem Biol* 2, 745-754.
42. Childs-Disney, J. L, and Disney, M. D. (2008) A simple ligation-based method to increase the information density in sequencing reactions used to deconvolute nucleic acid selections, *RNA* 14, 390-394.
43. Paul, D. J., Seedhouse, S. J., and Disney, M. D. (2009) Two-dimensional combinatorial screening and the RNA Privileged Space Predictor program efficiently identify aminoglycoside-RNA hairpin loop interactions, *Nucleic Acids Res* 37, 5894-5907.
44. Velagapudi, S. P., Seedhouse, S. J., and Disney, M. D. (2010) Structure-activity relationships through sequencing (StARTS) defines optimal and suboptimal RNA motif targets for small molecules, *Angew Chem Int Ed Engl* 49, 3816-3818.
45. Velagapudi, S. P., Seedhouse, S. J., French, J., and Disney, M. D. (2011) Defining the RNA Internal Loops Preferred by Benzimidazole Derivatives via 2D Combinatorial Screening and Computational Analysis, *J Am Chem Soc* 133, 10111-10118.
46. Wang, Y., and Rando, R. R. (1995) Specific binding of aminoglycoside antibiotics to RNA, *Chem. Biol,* 2, 281-290.
47. Warf, M. B., and Berglund, J. A. (2007) MBNL binds similar RNA structures in the CUG repeats of myotonic dystrophy and its pro-mRNA substrate cardiac troponin T, *Rna* 13, 2238-2251.
48. Tran, T., and Disney, M. D. (2010), *Biochemistry* 49, 1833-1842.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A dimeric r(CGG) binding compound of formula (II)

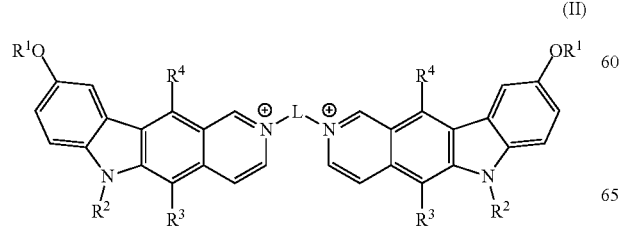

(II)

wherein
$R^1$ is H, (C1-C6)alkyl, or (C1-C6)alkanoyl;
$R^2$ is H, (C1-C6)alkyl, or (C1-C6)alkanoyl;
$R^3$ and $R^4$ are independently H, (C1-C6)alkyl, (C1-C6)haloalkyl, (C1-C6)alkoxyalkyl (C1-C6)haloalkoxyalkyl, or (C6-C10)aryl, wherein any alkyl, alkanoyl, alkoxy, or aryl group can be substituted with 0-3 J groups;
wherein J is any of halo, (C1-C6)alkyl, (C1-C6)alkoxy, (C1-C6)haloalkyl, hydroxy(C1-C6)alkyl, alkoxy (C1-C6)alkyl, (C1-C6)alkanoyl, (C1-C6)alkanoyloxy, cyano, nitro, azido, $R_2N$, $R_2NC(O)$, $R_2NC(O)O$, $R_2NC(O)NR$, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl;

R is independently at each occurrence H, (C1-C6)alkyl, or (C6-C10)aryl, wherein any alkyl or aryl group is substituted with 0-3 J;

and wherein L is a linker comprising a polypeptide backbone bonded by two respective nitrogen atoms thereof to a nitrogen atom of a respective 1,2,3-triazole group via a respective (C1-C6)alkylene group optionally further comprising a glycyl residue, each respective triazole group being bonded via a (C1-C6)alkylene group to the respective pyridinium nitrogen atom of each ellipticine scaffold; or a pharmaceutically acceptable salt thereof.

2. The compound of claim 1 wherein for the dimeric r(CGG) binding compound of formula (II), linker group L is a linker of formula (LI)

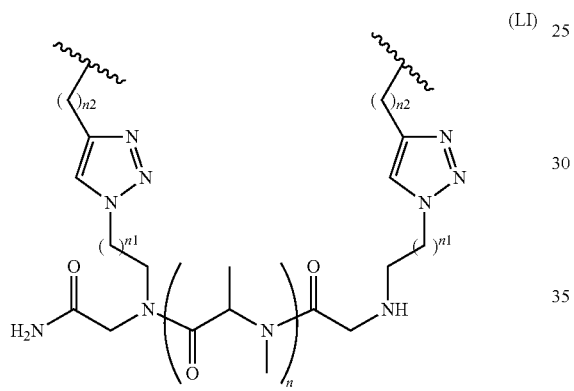

(LI)

wherein n=1, 2, 3, 4, 5, 6, 7, or 8; each independently selected n1=0, 1, 2, 3, 4, or 5; and each independently selected n2=1, 2, 3, 4, 5, or 6; and wherein a wavy line indicates a position of bonding to the respective pyridinium nitrogen atom of formula (II).

3. A pharmaceutical composition comprising a compound of claim 1 or 2 and a pharmaceutically acceptable excipient.

4. A method of inhibiting a messenger RNA molecule with a repeat r(CGG) sequence from binding to a protein with a binding affinity for a RNA hairpin loop comprising a non-Watson-Crick G-G nucleotide pair, comprising contacting the messenger RNA molecule having the repeat r(CGG) sequence and an effective amount or concentration of a dimeric r(CGG) binding compound of formula (II)

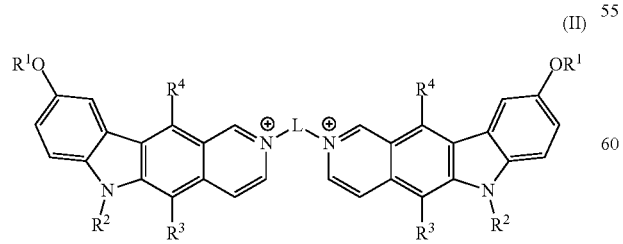

(II)

wherein
$R^1$ is H, (C1-C6)alkyl, or (C1-C6)alkanoyl;
$R^2$ is H, (C1-C6)alkyl, or (C1-C6)alkanoyl;

$R^3$ and $R^4$ are independently H, (C1-C6)alkyl, (C1-C6)haloalkyl, (C1-C6)alkoxyalkyl (C1-C6)haloalkoxyalkyl, or (C6-C10)aryl, wherein any alkyl, alkanoyl, alkoxy, or aryl group can be substituted with 0-3 J groups;

wherein J is any of halo, (C1-C6)alkyl, (C1-C6)alkoxy, (C1-C6)haloalkyl, hydroxy(C1-C6)alkyl, alkoxy(C1-C6)alkyl, (C1-C6)alkanoyl, (C1-C6)alkanoyloxy, cyano, nitro, azido, $R_2N$, $R_2NC(O)$, $R_2NC(O)O$, $R_2NC(O)NR$, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6)alkoxy, (C6-C10)aryloxy(C1-C6)alkyl, (C6-C10)aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered)heteroaryl(C1-C6)alkyl, (5- to 10-membered)heteroaryl(C1-C6)alkoxy, or (5- to 10-membered)heteroaroyl;

R is independently at each occurrence H, (C1-C6)alkyl, or (C6-C10)aryl, wherein any alkyl or aryl group is substituted with 0-3 J;

and wherein L is a linker comprising a polypeptide backbone bonded by two respective nitrogen atoms thereof to a nitrogen atom of a respective 1,2,3-triazole group via a respective (C1-C6)alkylene group optionally further comprising a glycyl residue, each respective triazole group being bonded via a (C1-C6)alkylene group to the respective pyridinium nitrogen atom of each ellipticine scaffold; or a pharmaceutically acceptable salt thereof.

5. The method of claim 4 wherein the repeat r(CGG) sequence is a $r(CGG)^{exp}$ sequence.

6. The method of claim 4 wherein $R^1$ is H, or wherein $R^2$ is H, or both.

7. The method of claim 4 wherein $R^3$ and $R^4$ are each methyl.

8. The method of claim 4 wherein for the dimeric r(CGG) binding compound of formula (II), linker group L is a linker of formula (LI)

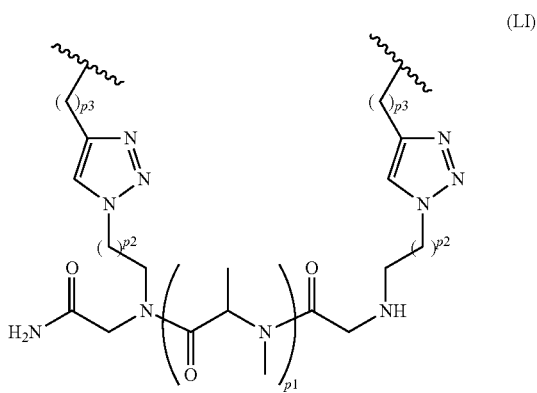

(LI)

wherein p1 =1, 2, 3, 4, 5, 6, 7, or 8; each independently selected p2=0, 1, 2, 3, 4, or 5; and each independently selected p3=1, 2, 3, 4, 5, or 6; and wherein a wavy line indicates a position of bonding to the respective pyridinium nitrogen atom of the compound of formula (II).

9. The method of claim 8 wherein the compound of formula (II) is of formula 2E-nNME

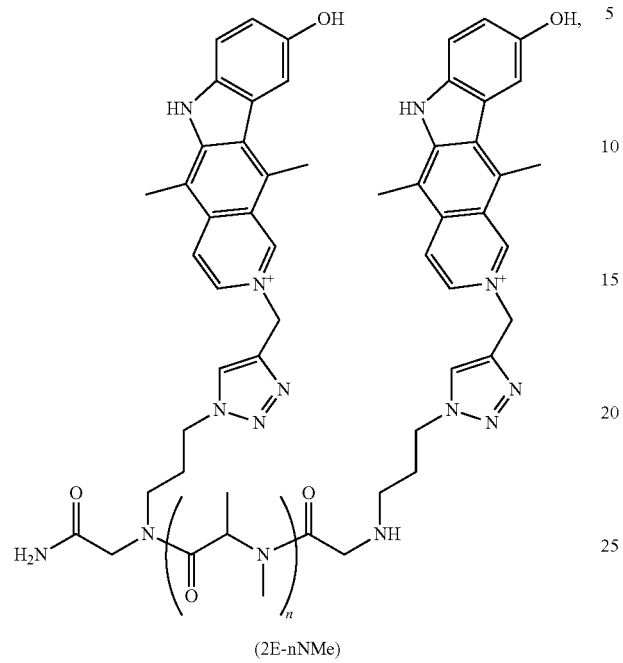

(2E-nNMe)

wherein n=1, 2, 3, 4, 5, 6, 7 or 8;
or a pharmaceutically acceptable salt thereof.

10. The method of claim 9 wherein the contacting is in vivo in a patient wherein the inhibiting is medically indicated for treatment of a condition.

11. The method of claim 10 wherein the patient is suffering from Fragile X-associated Tremor Ataxia Syndrome.

12. A method of treatment of Fragile X-associated Tremor Ataxia Syndrome, comprising administering to a patient afflicted therewith an effective amount or concentration of a dimeric r(CGG) binding compound of formula (II)

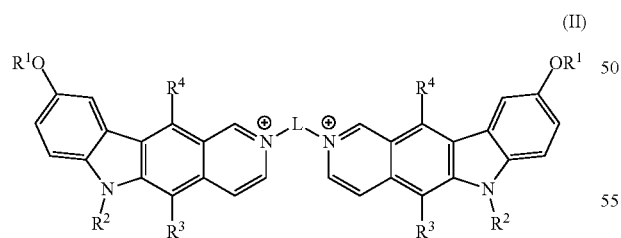

(II)

wherein
R$^1$ is H, (C1-C6)alkyl, or (C1-C6)alkanoyl;
R$^2$ is H, (C1-C6)alkyl, or (C1-C6)alkanoyl;
R$^3$ and R$^4$ are independently H, (C1-C6)alkyl, (C1-C6)haloalkyl, (C1-C6)alkoxyalkyl (C1-C6)haloalkoxyalkyl, or (C6-C10)aryl; wherein any alkyl, alkanoyl, alkoxy, or aryl group can be substituted with 0-3 J groups;

wherein J is any of halo, (C1-C6)alkyl, (C1-C6)alkoxy, (C1-C6)haloalkyl, hydroxy(C1-C6)alkyl, alkoxy (C1-C6)alkyl, (C1-C6)alkanoyl, (C1-C6)alkanoyloxy, cyano, nitro, azido, R$_2$N, R$_2$NC(O), R$_2$NC(O) O, R$_2$NC(O)NR, (C1-C6)alkenyl, (C1-C6)alkynyl, (C6-C10)aryl, (C6-C10)aryloxy, (C6-C10)aroyl, (C6-C10)aryl(C1-C6)alkyl, (C6-C10)aryl(C1-C6) alkoxy, (C6-C10)aryloxy(C1-C6)alkyl, (C6-C10) aryloxy(C1-C6)alkoxy, (3- to 9-membered)heterocyclyl, (3- to 9-membered)heterocyclyl(C1-C6)alkyl, (3- to 9-membered)heterocyclyl(C1-C6)alkoxy, (5- to 10-membered)heteroaryl, (5- to 10-membered) heteroaryl(C1-C6)alkyl, (5- to 10-membered)heteroaryl(C1-C6)alkoxy, or (5- to 10-membered)heteroaroyl;

R is independently at each occurrence H, (C1-C6)alkyl, or (C6-C10)aryl, wherein any alkyl or aryl group is substituted with 0-3 J;

and wherein L is a linker comprising a polypeptide backbone bonded by two respective nitrogen atoms thereof to a nitrogen atom of a respective 1,2,3-triazole group via a respective (C1-C6)alkylene group optionally further comprising a glycyl residue, each respective triazole group being bonded via a (C1-C6)alkylene group to the respective pyridinium nitrogen atom of each ellipticine scaffold; or a pharmaceutically acceptable salt thereof.

13. The method of claim 12 wherein R$^1$ is H.

14. The method of claim 12 wherein R$^2$ is H.

15. The method of claim 12 wherein R$^3$ and R$^4$ are each methyl.

16. The method of claim 12 wherein for the dimeric r(CGG) binding compound of formula (II), linker group L is a linker of formula (LI)

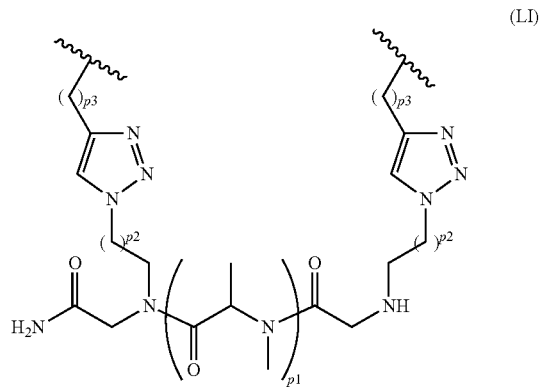

(LI)

wherein p1=1, 2, 3, 4, 5, 6, 7, or 8; each independently selected p2=0, 1, 2, 3, 4, or 5; and
each independently selected p3=1, 2, 3, 4, 5, or 6; and wherein a wavy line indicates a position of bonding to the respective pyridinium nitrogen atom of the compound of formula (II).

17. The method of claim 16 wherein the compound of formula (II) is of formula 2E-nNME
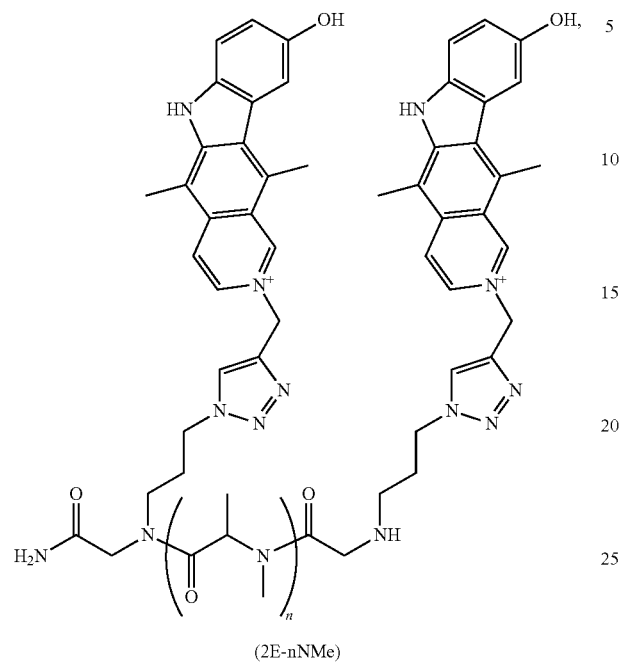
(2E-nNMe)
wherein n=1, 2, 3, 4, 5, 6, 7 or 8;
or a pharmaceutically acceptable salt thereof.
* * * * *